US009770598B2

(12) United States Patent
Malinowski et al.

(10) Patent No.: US 9,770,598 B2
(45) Date of Patent: Sep. 26, 2017

(54) SYSTEMS AND METHODS FOR MAKING AND USING IMPROVED CONNECTOR CONTACTS FOR ELECTRICAL STIMULATION SYSTEMS

(71) Applicant: Boston Scientific Neuromodulation Corporation, Valencia, CA (US)

(72) Inventors: Zdzislaw Bernard Malinowski, Castaic, CA (US); Jeffery Van Funderburk, Stevenson Ranch, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 43 days.

(21) Appl. No.: 14/835,511

(22) Filed: Aug. 25, 2015

(65) Prior Publication Data

US 2016/0059019 A1  Mar. 3, 2016

Related U.S. Application Data

(60) Provisional application No. 62/044,050, filed on Aug. 29, 2014.

(51) Int. Cl.
*A61N 1/05* (2006.01)
*A61N 1/375* (2006.01)
(Continued)

(52) U.S. Cl.
CPC ............ *A61N 1/3752* (2013.01); *A61N 1/05* (2013.01); *H01R 4/4881* (2013.01); *H01R 13/187* (2013.01); *H01R 24/58* (2013.01)

(58) Field of Classification Search
CPC ........ A61N 1/3752; A61N 1/05; H01R 24/58; H01R 13/187; H01R 4/4881
See application file for complete search history.

(56) References Cited

U.S. PATENT DOCUMENTS 4,602,624 A   7/1986  Naples et al.
4,630,611 A   12/1986 King
(Continued)

FOREIGN PATENT DOCUMENTS

EP      0580928 A1   2/1994
EP      0650694 B1   7/1998
(Continued)

*Primary Examiner* — Rex R Holmes
(74) *Attorney, Agent, or Firm* — Lowe Graham Jones PLLC; Bruce E. Black

(57) ABSTRACT

A connector for an implantable electrical medical device includes a connector lumen defined in an elongated connector housing and adapted for receiving a portion of a lead. Connector-contact assemblies are disposed in the connector lumen and adapted to couple to terminals of the lead when the lead is received by the connector lumen. Each of the connector-contact assemblies includes a contact body. An inner surface of the contact body defines an open center portion. A first base is disposed along a first end of the contact body, and a second base is disposed along an opposing second end of the contact body and is coupled to the first base. Biasing members are attached to the first base and extend towards the second base. The biasing members are not attached to the second base. When the lead is received by the connector lumen the biasing members physically contact the received lead.

20 Claims, 16 Drawing Sheets

(51) Int. Cl.
*H01R 4/48* (2006.01)
*H01R 13/187* (2006.01)
*H01R 24/58* (2011.01)

(56) References Cited

U.S. PATENT DOCUMENTS

| | | | |
|---|---|---|---|
| 4,744,370 | A | 5/1988 | Harris |
| 5,000,194 | A | 3/1991 | van den Honert et al. |
| 5,135,001 | A | 8/1992 | Sinofsky et al. |
| 5,374,285 | A | 12/1994 | Vaiani et al. |
| 5,458,629 | A | 10/1995 | Baudino et al. |
| 5,522,874 | A | 6/1996 | Gates |
| 5,711,316 | A | 1/1998 | Elsberry et al. |
| 5,713,922 | A | 2/1998 | King |
| 5,730,628 | A | 3/1998 | Hawkins |
| 5,800,350 | A | 9/1998 | Coppleson et al. |
| 5,843,148 | A | 12/1998 | Gijsbers et al. |
| 5,938,688 | A | 8/1999 | Schiff |
| 5,987,361 | A | 11/1999 | Mortimer |
| 6,018,684 | A | 1/2000 | Bartig et al. |
| 6,042,432 | A | 3/2000 | Hashazawa et al. |
| 6,134,478 | A | 10/2000 | Spehr |
| 6,161,047 | A | 12/2000 | King et al. |
| 6,167,311 | A | 12/2000 | Rezai |
| 6,181,969 | B1 | 1/2001 | Gord |
| 6,322,559 | B1 | 11/2001 | Daulton et al. |
| 6,510,347 | B2 | 1/2003 | Borkan |
| 6,516,227 | B1 | 2/2003 | Meadows et al. |
| 6,556,873 | B1 | 4/2003 | Smits |
| 6,564,078 | B1 | 5/2003 | Marino et al. |
| 6,609,029 | B1 | 8/2003 | Mann et al. |
| 6,609,032 | B1 | 8/2003 | Woods et al. |
| 6,678,564 | B2 | 1/2004 | Ketterl et al. |
| 6,741,892 | B1 | 5/2004 | Meadows et al. |
| 6,757,970 | B1 | 7/2004 | Kuzma et al. |
| 7,027,852 | B2 | 4/2006 | Helland |
| 7,047,084 | B2 | 5/2006 | Erickson et al. |
| 7,203,548 | B2 | 4/2007 | Whitehurst et al. |
| 7,244,150 | B1 | 7/2007 | Brase et al. |
| 7,292,890 | B2 | 11/2007 | Whitehurst et al. |
| 7,437,193 | B2 | 10/2008 | Parramon et al. |
| 7,489,971 | B1 | 2/2009 | Franz |
| 7,668,601 | B2 | 2/2010 | Hegland et al. |
| 7,672,734 | B2 | 3/2010 | Anderson et al. |
| 7,761,165 | B1 | 7/2010 | He et al. |
| 7,761,985 | B2 | 7/2010 | Hegland et al. |
| 7,822,482 | B2 | 10/2010 | Gerber |
| 7,840,188 | B2 | 11/2010 | Kurokawa |
| 7,848,802 | B2 | 12/2010 | Goetz |
| 7,856,707 | B2 | 12/2010 | Cole |
| 7,860,570 | B2 | 12/2010 | Whitehurst et al. |
| 7,949,395 | B2 | 5/2011 | Kuzma |
| 7,974,705 | B2 | 7/2011 | Zdeblick et al. |
| 7,974,706 | B2 | 7/2011 | Moffitt et al. |
| 7,979,140 | B2 | 7/2011 | Schulman |
| 8,000,808 | B2 | 8/2011 | Hegland et al. |
| 8,019,440 | B2 | 9/2011 | Kokones et al. |
| 8,036,755 | B2 | 10/2011 | Franz |
| 8,041,309 | B2 | 10/2011 | Kurokawa |
| 8,078,280 | B2 | 12/2011 | Sage |
| 8,099,177 | B2 | 1/2012 | Dahlberg |
| 8,175,710 | B2 | 5/2012 | He |
| 8,224,450 | B2 | 7/2012 | Brase |
| 8,225,504 | B2 | 7/2012 | Dye et al. |
| 8,295,944 | B2 | 10/2012 | Howard et al. |
| 8,321,025 | B2 | 11/2012 | Bedenbaugh |
| 8,359,107 | B2 | 1/2013 | Pianca et al. |
| 8,364,278 | B2 | 1/2013 | Pianca et al. |
| 8,391,985 | B2 | 3/2013 | McDonald |
| 8,583,237 | B2 | 11/2013 | Bedenbaugh |
| 8,688,235 | B1 | 4/2014 | Pianca et al. |
| 2001/0023368 | A1 | 9/2001 | Black et al. |
| 2002/0156513 | A1 | 10/2002 | Borkan |
| 2002/0183817 | A1 | 12/2002 | Van Venrooij et al. |
| 2005/0015130 | A1 | 1/2005 | Gill |
| 2005/0038489 | A1 | 2/2005 | Grill |
| 2005/0171587 | A1 | 8/2005 | Daglow et al. |
| 2006/0025841 | A1 | 2/2006 | McIntyre |
| 2006/0247697 | A1 | 11/2006 | Sharma et al. |
| 2007/0150036 | A1 | 6/2007 | Anderson |
| 2007/0168007 | A1 | 7/2007 | Kuzma et al. |
| 2007/0203546 | A1 | 8/2007 | Stone et al. |
| 2007/0219551 | A1 | 9/2007 | Honour et al. |
| 2008/0077186 | A1 | 3/2008 | Thompson et al. |
| 2008/0103580 | A1 | 5/2008 | Gerber |
| 2008/0114230 | A1 | 5/2008 | Addis |
| 2008/0215125 | A1 | 9/2008 | Farah et al. |
| 2008/0255647 | A1 | 10/2008 | Jensen et al. |
| 2009/0054941 | A1 | 2/2009 | Eggen et al. |
| 2009/0187222 | A1 | 7/2009 | Barker |
| 2009/0204192 | A1 | 8/2009 | Carlton et al. |
| 2009/0276021 | A1 | 11/2009 | Meadows et al. |
| 2010/0030298 | A1 | 2/2010 | Martens et al. |
| 2010/0036468 | A1 | 2/2010 | Decre et al. |
| 2010/0076535 | A1 | 3/2010 | Pianca et al. |
| 2010/0077606 | A1 | 4/2010 | Black et al. |
| 2010/0082076 | A1 | 4/2010 | Lee et al. |
| 2010/0094387 | A1 | 4/2010 | Pianca et al. |
| 2010/0100152 | A1 | 4/2010 | Martens et al. |
| 2010/0268298 | A1 | 10/2010 | Moffitt et al. |
| 2010/0269338 | A1 | 10/2010 | Dye |
| 2010/0269339 | A1 | 10/2010 | Dye et al. |
| 2010/0287770 | A1 | 11/2010 | Dadd et al. |
| 2011/0004267 | A1 | 1/2011 | Meadows |
| 2011/0005069 | A1 | 1/2011 | Pianca |
| 2011/0047795 | A1 | 3/2011 | Turner et al. |
| 2011/0056076 | A1 | 3/2011 | Hegland et al. |
| 2011/0077699 | A1 | 3/2011 | Swanson et al. |
| 2011/0078900 | A1 | 4/2011 | Pianca et al. |
| 2011/0130803 | A1 | 6/2011 | McDonald |
| 2011/0130816 | A1 | 6/2011 | Howard et al. |
| 2011/0130817 | A1 | 6/2011 | Chen |
| 2011/0130818 | A1 | 6/2011 | Chen |
| 2011/0131808 | A1 | 6/2011 | Gill |
| 2011/0238129 | A1 | 9/2011 | Moffitt et al. |
| 2011/0245903 | A1 | 10/2011 | Schulte et al. |
| 2011/0301665 | A1 | 12/2011 | Mercanzini et al. |
| 2011/0313500 | A1 | 12/2011 | Barker et al. |
| 2012/0016378 | A1 | 1/2012 | Pianca et al. |
| 2012/0046710 | A1 | 2/2012 | DiGiore et al. |
| 2012/0071949 | A1 | 3/2012 | Pianca et al. |
| 2012/0165911 | A1 | 6/2012 | Pianca |
| 2012/0185019 | A1* | 7/2012 | Schramm ............ A61N 1/3752 607/72 |
| 2012/0197375 | A1 | 8/2012 | Pianca et al. |
| 2012/0203316 | A1 | 8/2012 | Moffitt et al. |
| 2012/0203320 | A1 | 8/2012 | DiGiore et al. |
| 2012/0203321 | A1 | 8/2012 | Moffitt et al. |
| 2012/0316615 | A1 | 12/2012 | DiGiore et al. |
| 2013/0053864 | A1* | 2/2013 | Geroy ................. A61N 1/05 606/129 |
| 2013/0105071 | A1 | 5/2013 | DiGiore et al. |
| 2013/0109254 | A1 | 5/2013 | Klardie et al. |
| 2013/0116754 | A1 | 5/2013 | Sharma et al. |
| 2013/0197424 | A1 | 8/2013 | Bedenbaugh |
| 2013/0197602 | A1 | 8/2013 | Pianca et al. |
| 2013/0261684 | A1 | 10/2013 | Howard |
| 2013/0317587 | A1 | 11/2013 | Barker |
| 2013/0325091 | A1 | 12/2013 | Pianca et al. |
| 2014/0039587 | A1 | 2/2014 | Romero |
| 2014/0088666 | A1 | 3/2014 | Goetz et al. |
| 2014/0142671 | A1 | 5/2014 | Moffitt et al. |
| 2014/0180375 | A1 | 6/2014 | Pianca et al. |
| 2014/0353001 | A1 | 12/2014 | Romero et al. |
| 2014/0358207 | A1 | 12/2014 | Romero |
| 2014/0358208 | A1 | 12/2014 | Howard et al. |
| 2014/0358209 | A1 | 12/2014 | Romero et al. |
| 2014/0358210 | A1 | 12/2014 | Howard et al. |
| 2015/0018915 | A1 | 1/2015 | Leven |
| 2015/0021817 | A1 | 1/2015 | Romero et al. |
| 2015/0045864 | A1 | 2/2015 | Howard |

(56) References Cited

U.S. PATENT DOCUMENTS

2015/0066120 A1    3/2015   Govea
2015/0151113 A1    6/2015   Govea et al.

FOREIGN PATENT DOCUMENTS

| EP | 0832667 B1 | 2/2004 |
|----|------------|--------|
| EP | 1181947 B1 | 1/2006 |
| EP | 2092952 A1 | 8/2009 |
| WO | 9732628 A1 | 9/1997 |
| WO | 9955411 A3 | 2/2000 |
| WO | 0038574 A1 | 7/2000 |
| WO | 2001058520 A1 | 8/2001 |
| WO | 02068042 A1 | 9/2002 |
| WO | 2004045707 A1 | 6/2004 |
| WO | 2008018067 A2 | 2/2008 |
| WO | 2008053789 A1 | 5/2008 |
| WO | 2008100841 | 8/2008 |
| WO | 2009025816 A1 | 2/2009 |
| WO | 2009102536 A1 | 8/2009 |
| WO | 2013162775 A2 | 10/2013 |
| WO | 2014018092 A1 | 1/2014 |

\* cited by examiner

SYSTEMS AND METHODS FOR MAKING AND USING IMPROVED CONNECTOR CONTACTS FOR ELECTRICAL STIMULATION SYSTEMS

CROSS-REFERENCE TO RELATED APPLICATIONS

This application claims the benefit under 35 U.S.C. §119 (e) of U.S. Provisional Patent Application Ser. No. 62/044,050, filed Aug. 29, 2014, which is incorporated herein by reference.

FIELD

The present invention is directed to the area of implantable electrical stimulation systems and methods of making and using the systems. The present invention is also directed to implantable electrical stimulation systems having connectors with improved connector contacts, as well as methods of making and using the connectors, connector contacts, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat incontinence, as well as a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, a connector for an implantable electrical medical device includes an elongated connector housing having a first end and an opposing second end. A connector lumen is defined in the connector housing and is configured and arranged for receiving a proximal portion of a lead or lead extension. Connector-contact assemblies are disposed in the connector lumen and are each configured and arranged to couple to a terminal of the lead or lead extension when the proximal portion of the lead or lead extension is received by the connector lumen. Each of the connector-contact assemblies includes a contact body having a first end, an opposing second end, an inner surface, and an outer surface. The inner surface of the contact body defines an open center portion having an inner diameter. A first base is disposed along the first end of the contact body, and a second base is disposed along the second end of the contact body and is coupled to the first base. Biasing members are attached to the first base and extend towards the second base. The biasing members are not attached to the second base. When the proximal portion of the lead or lead extension is received by the connector lumen the biasing members physically contact the received lead or lead extension. Connector conductors are coupled to the connector-contact assemblies and extend along the connector housing.

In at least some embodiments, for each of the connector-contact assemblies, the second base is coupled to the first base by at least one rigid support member. In at least some embodiments, each of the connector-contact assemblies includes at least eight biasing members. In at least some embodiments, each of the connector-contact assemblies includes no more than sixteen biasing members. In at least some embodiments, for each of the connector-contact assemblies, the biasing members each include at least one bend that extends into the open center portion of the contact body and that narrows the inner diameter of the open center portion.

In at least some embodiments, a lead assembly includes: a lead with a lead body with a proximal portion, a distal portion, and a longitudinal length; electrodes disposed on the distal portion of the lead body; terminals disposed on the proximal portion of the lead body; and lead conductors electrically coupling the electrodes to the terminals. A lead extension has a proximal portion and a distal portion. The above-described connector is disposed along the distal portion of the lead extension. The proximal portion of the lead is configured and arranged for insertion into the connector lumen of the connector.

In at least some embodiments, an electrical stimulating system includes the above-described lead assembly. A control module is coupleable to the proximal portion of the lead extension of the lead assembly. The control module includes a housing and an electronic subassembly disposed in the housing.

In at least some embodiments, an electrical stimulating system includes a lead having: a lead body with a proximal portion, a distal portion, and a longitudinal length; electrodes disposed along the distal portion of the lead; terminals disposed along the proximal portion of the lead; and lead conductors electrically coupling the electrodes to the terminals. A control module is electrically coupleable to the electrodes. The control module includes a housing and an electronic subassembly disposed in the housing. The above-described connector is coupled directly to the control module. The proximal portion of the lead is configured and arranged for insertion into the connector lumen of the connector.

In another embodiment, a connector for an implantable electrical medical device includes an elongated connector housing having a first end and an opposing second end. A connector lumen is defined in the connector housing. The connector lumen is configured and arranged for receiving a proximal portion of a lead or lead extension. Connector-contact assemblies are disposed in the connector housing. Each of the connector-contact assemblies includes a contact housing having a first end, an opposing second end, a longitudinal length, an inner surface, and an outer surface. The inner surface of the contact housing defines an open center portion having an inner diameter, The open center portion forms a portion of the connector lumen. A connector contact is disposed in the open center portion of the contact housing. The connector contact includes biasing members extending longitudinally outwardly away from the first end of the contact housing and bending back around and into the open center portion of the contact housing. When the proximal portion of the lead or lead extension is received by the connector lumen the biasing members physically contact the received lead or lead extension. Connector conductors coupled to the connector-contact assemblies and extend along the connector housing.

In at least some embodiments, for each of the connector-contact assemblies, the contact housing and the corresponding connector contact are formed entirely from a single piece of electrically-conductive material. In at least some embodiments, for each of the connector-contact assemblies, the biasing members extend along an entire length of the open center portion of the contact housing. In at least some embodiments, for each of the connector-contact assemblies, the biasing members each include a bend that extends into the open center portion of the contact housing and that narrows the inner diameter of the open center portion. In at least some embodiments, for the each of the connector-contact assemblies, the contact housing is electrically coupled to the connector housing.

In yet another embodiment, a connector for an implantable electrical medical device includes an elongated connector housing having a first end and an opposing second end. A connector lumen is defined in the connector housing. The connector lumen is configured and arranged for receiving a proximal portion of a lead or lead extension. Connector-contact assemblies are disposed in the connector housing. Each of the connector-contact assemblies includes a contact housing having a first end portion, a second end portion, an inner surface, and an outer surface. The inner surface of the contact housing defines an open center portion having a circumference. The open center portion of the contact housing forms a portion of the connector lumen. The open center portion has a first inner diameter along the first end portion and a second inner diameter along the second end portion. The second inner diameter is larger than the first inner diameter. A connector contact is disposed in the open center portion of the contact housing. The connector contact includes a first base disposed along the first end portion of the contact housing and around the circumference of the open center portion of the contact housing. The connector further includes a second base disposed along the second end portion of the contact housing and around the circumference of the open center portion of the contact housing. Biasing members extend along the inner surface of the contact housing and attach the first base to the second base. When the proximal portion of the lead or lead extension is received by the connector lumen the biasing members physically contact the received lead or lead extension. Connector conductors are coupled to the connector-contact assemblies and extend along the connector housing.

In still yet another embodiment, a method of forming a connector-contact assembly includes cutting a contact housing and a pre-connector contact from electrically-conductive tubing. The contact housing defines an open center portion. The pre-connector contact includes biasing members. The biasing members of the pre-connector contact are bent to form a connector contact. The connector contact is inserted into the open center portion of the contact housing.

In at least some embodiments, bending the biasing members of the pre-connector contact to form a connector contact includes forming a bend that narrows an inner diameter of the open center portion when the connector contact is inserted into the open center portion of the contact housing. In at least some embodiments, inserting the connector contact into the contact lumen of the contact housing includes pressing the connector contact into the contact lumen of the contact housing. In at least some embodiments, inserting the connector contact into an open center portion of the contact housing includes maintaining the connector contact within the open center portion of the contact housing solely by an interference fit.

In at least some embodiments, the above-described method further includes at least one of welding or adhesively-affixing the connector contact to the contact housing. In at least some embodiments, the above-described method further includes inserting the connector-contact assembly into a connector of an implantable electrical stimulation system.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation systems having connectors with improved connector contacts, as well as methods of making and using, the connectors, connector contacts, and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, deep brain stimulation leads, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; and 8,391,985; U.S. Patent Applications Publication Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; and 2013/0105071; and U.S. patent application Ser. Nos. 12/177,823 and 13/750,725, all of which are incorporated by reference.

Figure 1:
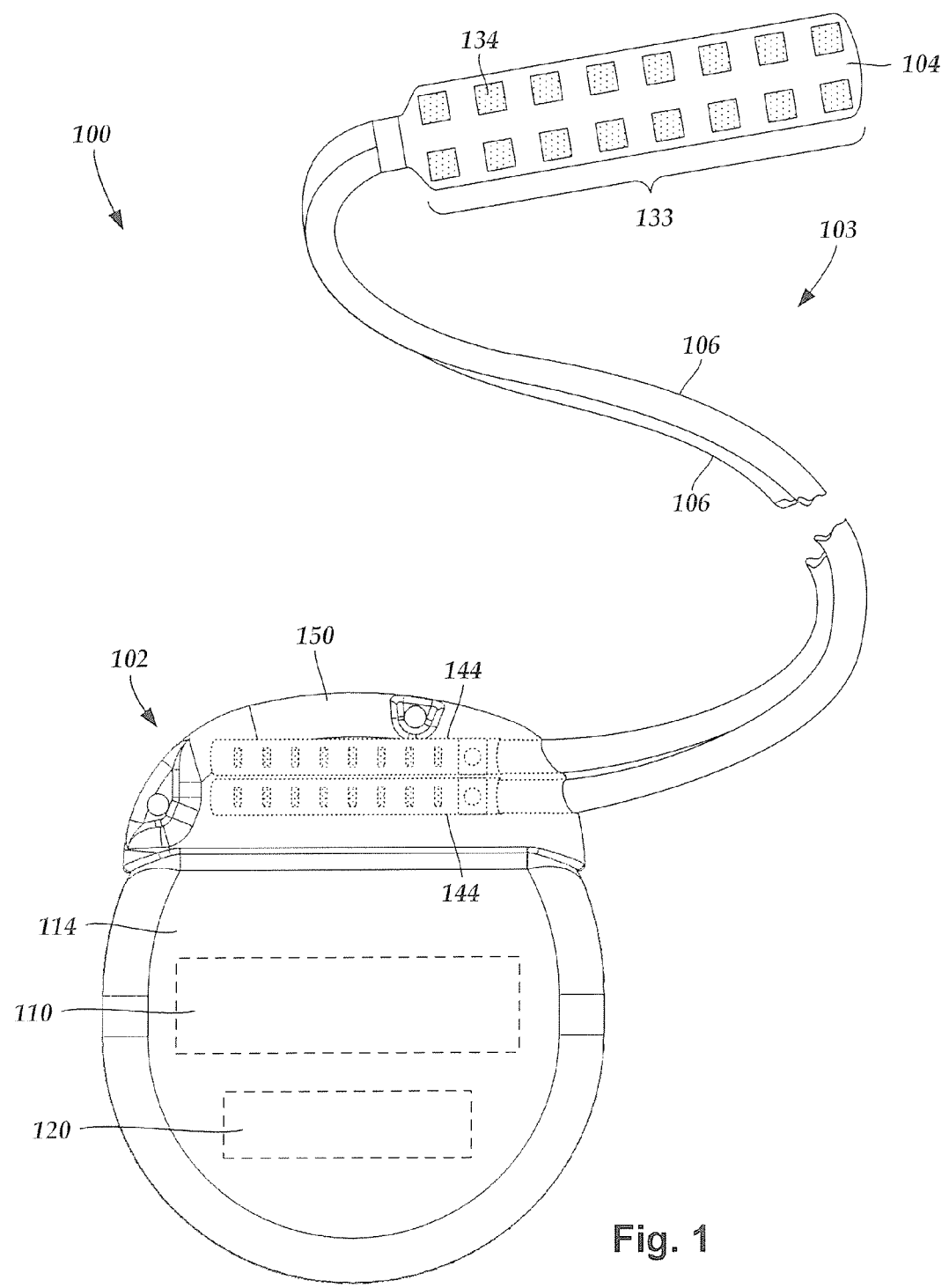
FIG. 1 is a schematic view of one embodiment of an implantable medical device that includes a paddle body coupled to a control module via lead bodies, according to the invention.

FIG. 1 illustrates schematically one embodiment of an electrical stimulation system 100. The electrical stimulation system includes a control module (e.g., a stimulator or pulse generator) 102 and a lead 103. The lead 103 including a paddle body 104 and one or more lead bodies 106 coupling the control module 102 to the paddle body 104. The paddle body 104 and the one or more lead bodies 106 form the lead 103. The paddle body 104 typically includes a plurality of electrodes 134 that form an array of electrodes 133. The control module 102 typically includes an electronic subassembly 110 and an optional power source 120 disposed in a sealed housing 114. In FIG. 1, two lead bodies 106 are shown coupled to the control module 102.

The control module 102 typically includes one or more connectors 144 into which the proximal end of the one or more lead bodies 106 can be plugged to make an electrical connection via connector contacts (e.g., 316 in FIG. 3A) disposed in the connector 144 and terminals (e.g., 310 in FIG. 3A) on each of the one or more lead bodies 106. The connector contacts are coupled to the electronic subassembly 110 and the terminals are coupled to the electrodes 134. In FIG. 1, two connectors 144 are shown.

The one or more connectors 144 may be disposed in a header 150. The header 150 provides a protective covering over the one or more connectors 144. The header 150 may be formed using any suitable process including, for example, casting, molding (including injection molding), and the like. In addition, one or more lead extensions 324 (see FIG. 3C) can be disposed between the one or more lead bodies 106 and the control module 102 to extend the distance between the one or more lead bodies 106 and the control module 102.

Figure 2:
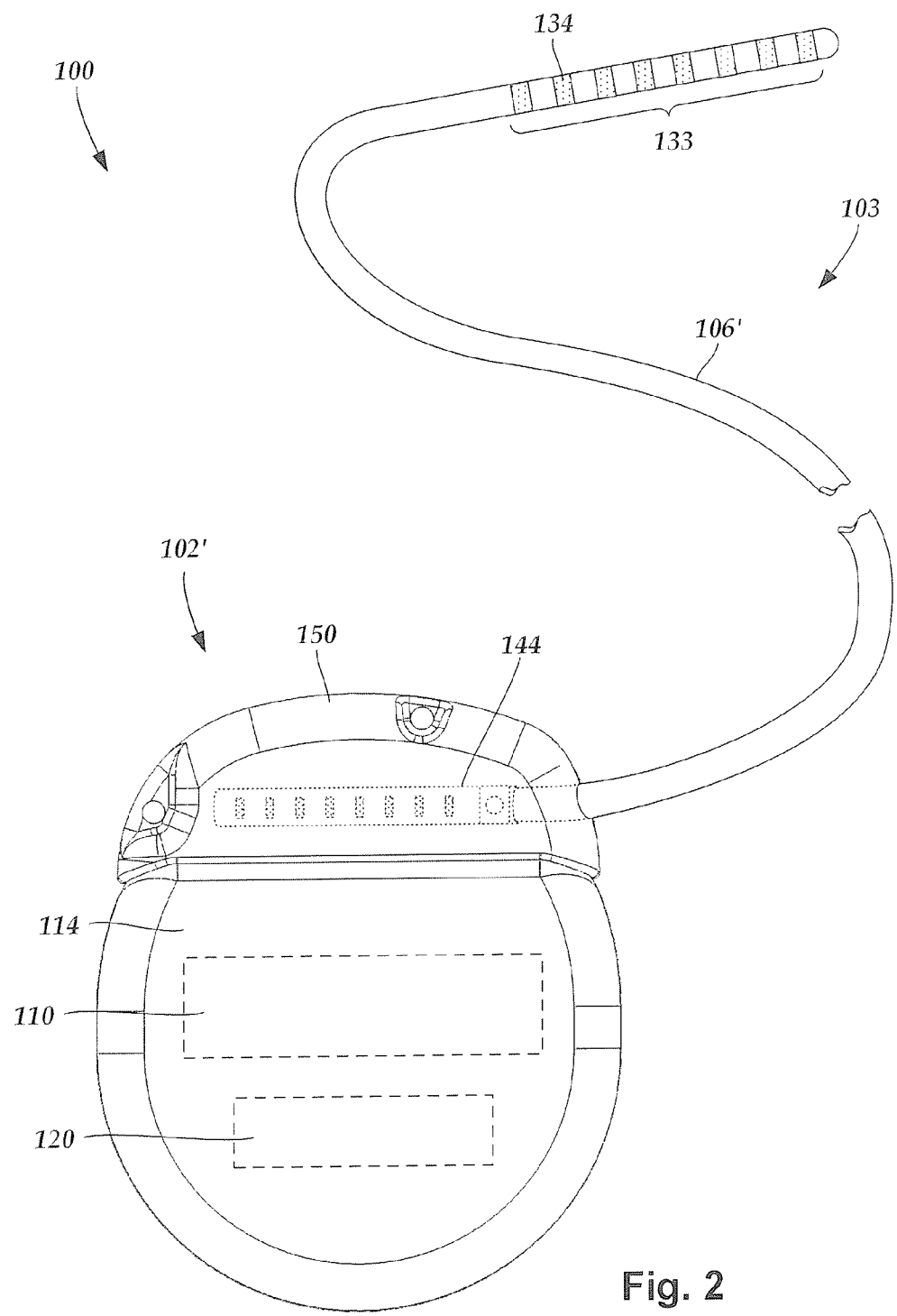
FIG. 2 is a schematic view of another embodiment of an implantable medical device that includes a percutaneous lead body coupled to a control module via a lead body, according to the invention.

It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of a lead body 106' forming a percutaneous lead 103, as illustrated in FIG. 2. The percutaneous lead may be isodiametric along the length of the lead body 106". The lead body 106' can be coupled with a control module 102' with a single connector 144.

The electrical stimulation system or components of the electrical stimulation system, including one or more of the lead bodies 106, the control module 102, and, in the case of a paddle lead, the paddle body 104, are typically implanted into the body of a patient. The electrical stimulation system can be used for a variety of applications including, but not limited to, spinal cord stimulation, brain stimulation, neural stimulation, muscle activation via stimulation of nerves innervating muscle, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, titanium, or rhenium.

The number of electrodes 134 in the array of electrodes 133 may vary. For example, there can be two, three, four, five, six, seven, eight, nine, ten, eleven, twelve, thirteen, fourteen, fifteen, sixteen, or more electrodes 134. As will be recognized, other numbers of electrodes 134 may also be used. In FIG. 1, sixteen electrodes 134 are shown. The electrodes 134 can be formed in any suitable shape including, for example, round, oval, triangular, rectangular, pentagonal, hexagonal, heptagonal, octagonal, or the like.

The electrodes of the paddle body 104 or one or more lead bodies 106 are typically disposed in, or separated by, a non-conductive, biocompatible material including, for example, silicone, polyurethane, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead 103 to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A) are typically disposed at the proximal end of the one or more lead bodies 106 for connection to corresponding conductive contacts (e.g., 316 in FIG. 3A) in connectors (e.g., 144 in FIG. 1) disposed on, for example, the control module 102 (or to other devices, such as conductive contacts on a lead extension, an operating room cable, a splitter, an adaptor, or the like).

Conductive wires (not shown) extend from the terminals (e.g., 310 in FIG. 3A) to the electrodes 134. Typically, one or more electrodes 134 are electrically coupled to a terminal (e.g., 310 in FIG. 3A). In some embodiments, each terminal (e.g., 310 in FIG. 3A) is only coupled to one electrode 134.

The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. The one or more lumens may, optionally, be flushed continually, or on a regular basis, with saline, epidural fluid, or the like. The one or more lumens can be permanently or removably sealable at the distal end.

As discussed above, the one or more lead bodies 106 may be coupled to the one or more connectors 144 disposed on the control module 102. The control module 102 can include any suitable number of connectors 144 including, for example, two three, four, five, six, seven, eight, or more connectors 144. It will be understood that other numbers of connectors 144 may be used instead. In FIG. 1, each of the two lead bodies 106 includes eight terminals that are shown coupled with eight conductive contacts disposed in a different one of two different connectors 144.

Figure 3A:
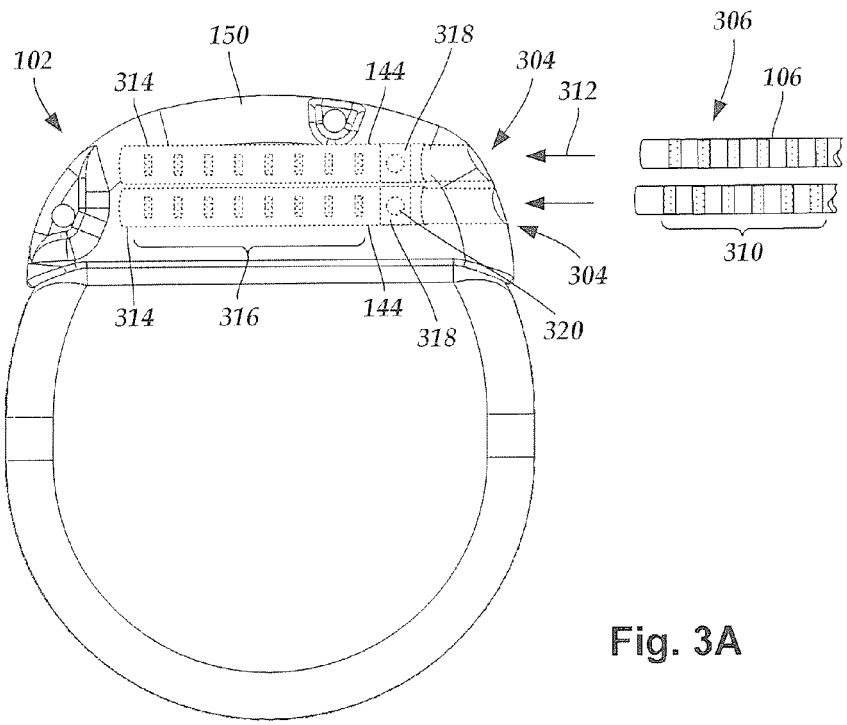
FIG. 3A is a schematic view of one embodiment of a plurality of connectors disposed in the control module of FIG. 1, the connectors configured and arranged to receive the proximal portions of the lead bodies of FIG. 1, according to the invention.
Figure 3B:
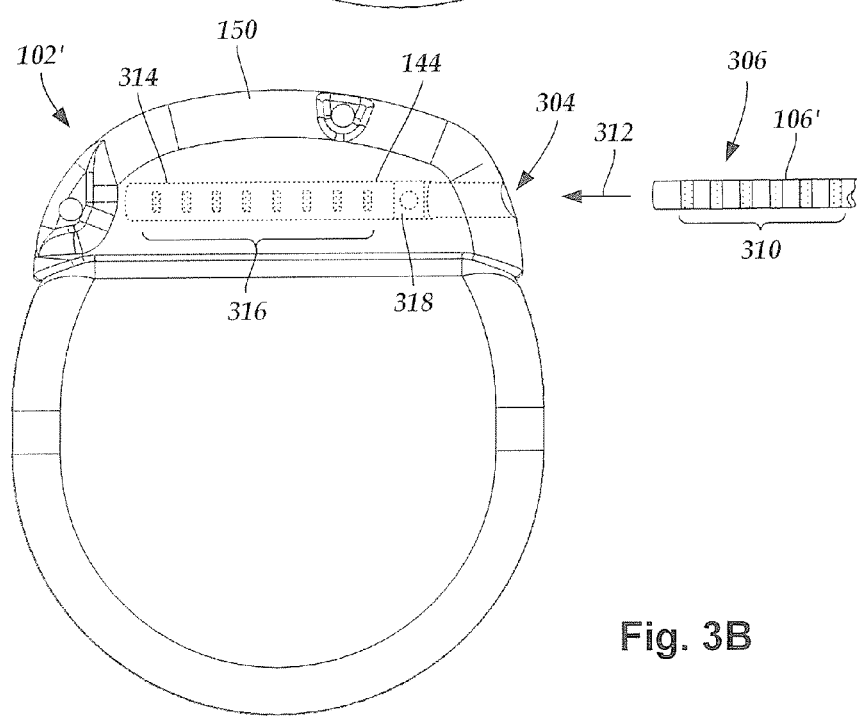
FIG. 3B is a schematic view of one embodiment of a connector disposed in the control module of FIG. 2, the connector configured and arranged to receive the proximal portion of one of the lead body of FIG. 2, according to the invention.

FIG. 3A is a schematic side view of one embodiment of a plurality of connectors 144 disposed on the control module 102. In at least some embodiments, the control module 102 includes two connectors 144. In at least some embodiments, the control module 102 includes four connectors 144. In FIG. 3A, proximal ends 306 of the plurality of lead bodies 106 are shown configured and arranged for insertion to the control module 102. FIG. 3B is a schematic side view of one embodiment of a single connector 144 disposed on the control module 102'. In FIG. 3B, the proximal end 306 of the single lead body 106' is shown configured and arranged for insertion to the control module 102'.

In FIGS. 3A and 3B, the one or more connectors 144 are disposed in the header 150. In at least some embodiments, the header 150 defines one or more lumens 304 into which the proximal end(s) 306 of the one or more lead bodies 106/106' with terminals 310 can be inserted, as shown by directional arrows 312, in order to gain access to the connector contacts disposed in the one or more connectors 144.

The one or more connectors 144 each include a connector housing 314 and a plurality of connector contacts 316 disposed therein. Typically, the connector housing 314 provides access to the plurality of connector contacts 316 via the lumen 304. In at least some embodiments, one or more of the connectors 144 further includes a retaining element 318 configured and arranged to fasten the corresponding lead body 106/106' to the connector 144 when the lead body 106/106' is inserted into the connector 144 to prevent undesired detachment of the lead body 106/106' from the connector 144. For example, the retaining element 318 may include an aperture 320 through which a fastener (e.g., a set screw, pin, or the like) may be inserted and secured against an inserted lead body 106/106'.

When the one or more lead bodies 106/106' are inserted into the one or more lumens 304, the connector contacts 316 can be aligned with the terminals 310 disposed on the one or more lead bodies 106/106' to electrically couple the control module 102 to the electrodes (134 of FIG. 1) disposed at a distal end of the one or more lead bodies 106. Examples of connectors in control modules are found in, for example, U.S. Pat. Nos. 7,244,150 and 8,224,450, which are incorporated by reference.

Figure 3C:
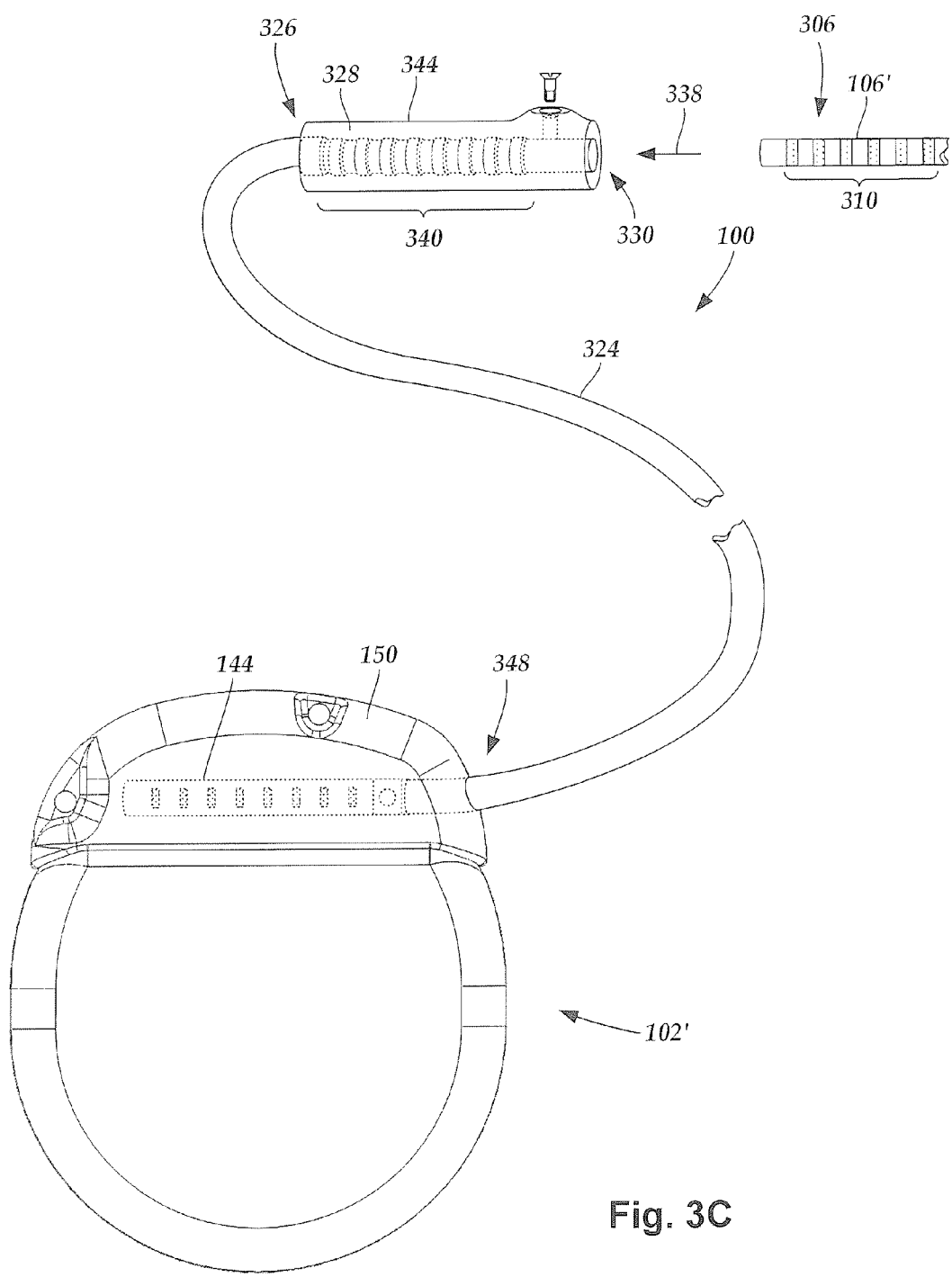
FIG. 3C is a schematic view of one embodiment of a proximal portion of the lead body of FIG. 2, a lead extension, and the control module of FIG. 2, the lead extension configured and arranged to couple the lead body to the control module, according to the invention.

In at least some embodiments, the electrical stimulation system includes one or more lead extensions. The one or more lead bodies 106/106' can be coupled to one or more lead extensions which, in turn, are coupled to the control module 102/102'. In FIG. 3C, a lead extension connector 322 is disposed on a lead extension 324. The lead extension connector 322 is shown disposed at a distal end 326 of the lead extension 324. The lead extension connector 322 includes a connector housing 344. The connector housing 344 defines at least one lumen 330 into which a proximal end 306 of the lead body 106' with terminals 310 can be inserted, as shown by directional arrow 338. The lead extension connector 322 also includes a plurality of connector contacts 340. When the lead body 106' is inserted into the lumen 330, the connector contacts 340 disposed in the connector housing 344 can be aligned with the terminals 310 on the lead body 106 to electrically couple the lead extension 324 to the electrodes (134 of FIG. 1) disposed at a distal end (not shown) of the lead body 106'.

The proximal end of a lead extension can be similarly configured and arranged as a proximal end of a lead body. The lead extension 324 may include a plurality of conductive wires (not shown) that electrically couple the connector contacts 340 to terminal on a proximal end 348 of the lead extension 324. The conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a lead extension connector disposed in another lead extension. In other embodiments (as shown in FIG. 3C), the proximal end 348 of the lead extension 324 is configured and arranged for insertion into the connector 144 disposed on the control module 102'.

It will be understood that the control modules 102/102' can receive either lead bodies 106/106' or lead extensions 324. It will also be understood that the electrical stimulation system 100 can include a plurality of lead extensions 224. For example, each of the lead bodies 106 shown in FIGS. 1 and 3A can, alternatively, be coupled to a different lead extension 224 which, in turn, are each coupled to different ports of a two-port control module, such as the control module 102 of FIGS. 1 and 3A.

Figure 4:
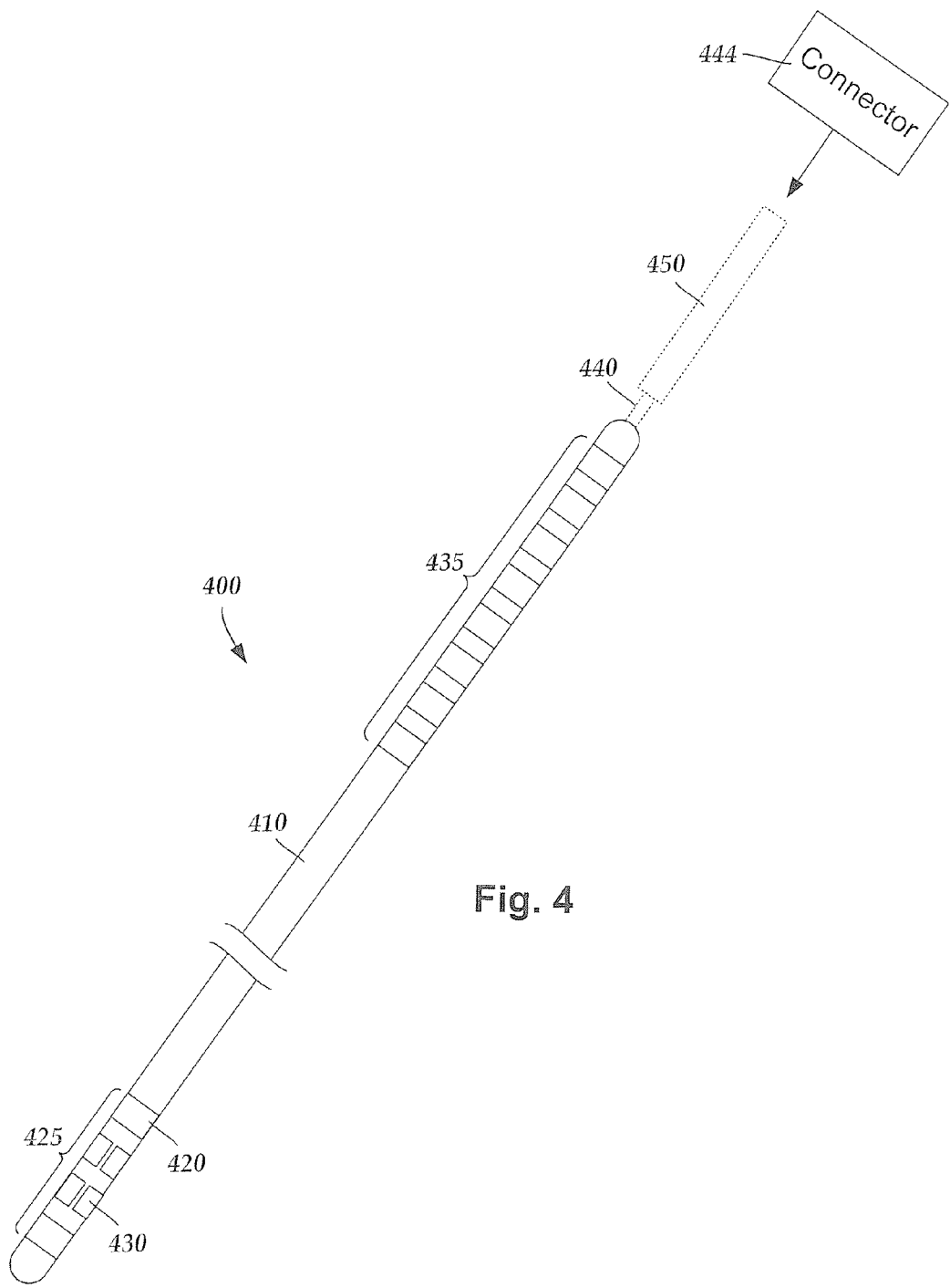
FIG. 4 is a schematic side view of yet another embodiment of an implantable medical device for brain stimulation, according to the invention.

Turning to FIG. 4, in the case of deep brain stimulation, the lead may include stimulation electrodes, recording electrodes, or a combination of both. At least some of the stimulation electrodes, recording electrodes, or both are provided in the form of segmented electrodes that extend only partially around the circumference of the lead. These segmented electrodes can be provided in sets of electrodes, with each set having electrodes radially distributed about the lead at a particular longitudinal position.

In at least some embodiments, a practitioner may determine the position of the target neurons using recording electrode(s) and then position the stimulation electrode(s) accordingly. In some embodiments, the same electrodes can be used for both recording and stimulation. In some embodiments, separate leads can be used; one with recording electrodes which identify target neurons, and a second lead with stimulation electrodes that replaces the first after target neuron identification. In some embodiments, the same lead may include both recording electrodes and stimulation electrodes or electrodes may be used for both recording and stimulation.

FIG. 4 illustrates one embodiment of a device 400 for brain stimulation. The device includes a lead 410, a plurality of electrodes 425 disposed at least partially about a circumference of the lead 410, a plurality of terminals 435, a connector 444 for connection of the electrodes to a control unit, and a stylet 440 for assisting in insertion and positioning of the lead in the patient's brain. The stylet 440 can be made of a rigid material. Examples of suitable materials for the stylet include, but are not limited to, tungsten, stainless steel, and plastic. The stylet 440 may have a handle 450 to assist insertion into the lead 410, as well as rotation of the stylet 440 and lead 410. The connector 444 fits over a proximal end of the lead 410, preferably after removal of the stylet 440.

Figure 5:
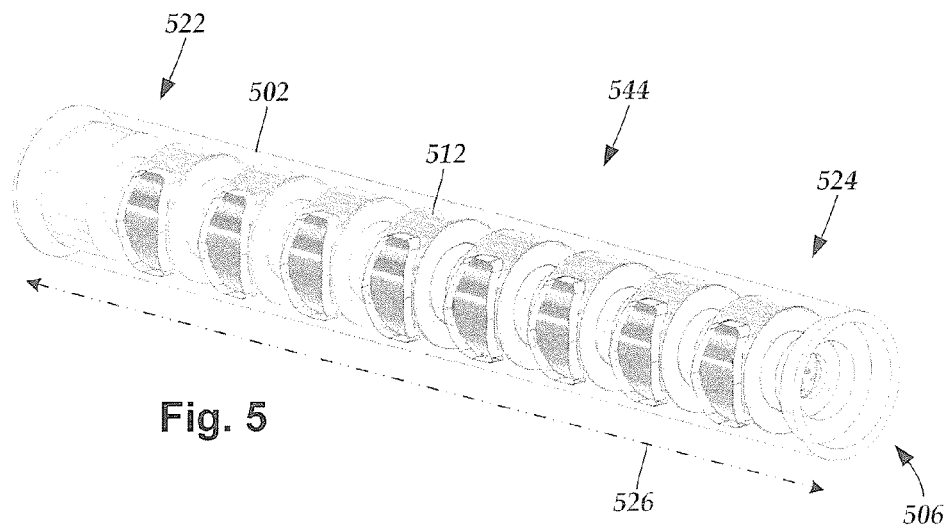
FIG. 5 is a schematic perspective view of one embodiment of a connector suitable for use with the implantable medical devices of FIGS. 1, 2, and 4, according to the invention.

Turning to FIG. 5, connector contacts (see e.g., 316 in FIGS. 3A-3B; and 340 in FIG. 3C) for electrical stimulation systems can be disposed in various types of connectors (see e.g., 144 in FIGS. 1-3C; 344 in FIG. 3C; and 44 in FIG. 4) that, in turn, are disposed along various types of implantable medical devices including, for example, control modules, lead extensions, adaptors, or the like. At least some conventional connectors use connector contacts formed from coiled springs adapted to completely encircle terminals of inserted elongated members (e.g., leads, lead extensions, or the like) when making electrical connection with those terminals. Such connector contacts can be labor-intensive to form and to dispose in connectors. Consequently, it would be advantageous to utilize connectors with connector contacts that are cheaper to manufacture, while continuing to provide a robust electrical connection between the connector contacts and inserted terminals of elongated members.

As herein described, an improved connector may be used with implantable medical devices, such as electrical stimulation systems. The improved connector includes connector contacts with biasing members that are biased to maintain electrical contact with terminals of received elongated members. In some embodiments, the connector contacts are disposed in individual contact housings arranged in the connector. In other embodiments, the connector contacts are disposed in the connector without being disposed in individual contact housings (i.e., the connector contacts are housing-less). The connector contacts may, optionally, be formed from tubing.

FIG. 5 illustrates, in perspective view, one embodiment of a connector 544 suitable for use with an implantable medical device. The connector 544 can be disposed, for example, on a control module, lead extension, adaptor, or the like. The connector 544 has a first end 522, an opposing second end 524, and a longitudinal length 526. The connector 544 includes an elongated connector housing 502 that defines a connector lumen 506 suitable for receiving a portion of an elongated member, such as a lead, lead extension, or the like. In FIG. 5, the connector lumen 506 is defined along the second end 524 of the connector 544 and extends along at least 25%, 50%, 75%, 90%, of the longitudinal length 526 of the connector 544. The first end 522 of the connector 544 can be either open or closed.

Multiple connector-contact assemblies, such as connector-contact assembly 512, are disposed along the connector housing 502 such that the connector-contact assemblies 512 are exposed to the connector lumen 506. The connector-contact assemblies 512 are configured into a longitudinally-spaced-apart arrangement along the connector housing 502 that facilitates making electrical contact with terminals disposed along inserted elongated members (e.g., leads, lead extensions, or the like). Connector conductors (not shown) are electrically coupled to the connector-contact assemblies 512 and couple to one or more coupled implantable medical devices (e.g., a control module, or the like).

The connector housing 502 can be formed in any shape suitable for receiving an elongated member into the connector lumen. In at least some embodiments, the connector maintains a constant shape along the entire longitudinal length of the connector. In at least some embodiments, the connector maintains a constant size along the entire longitudinal length of the connector.

It will be understood that the connector 544 is an exemplary connector for an implantable electrical stimulation system and is not meant to be limiting. The below-described connector-contact assemblies are suitable for being incorporated into the connector 544. Additionally, the below-described connector-contact assemblies can be incorporated into other connectors suitable for use with implantable electrical stimulation systems.

Multiple different embodiments of connector-contact assemblies are described below. The connector-contact assemblies include different embodiments of connector contacts. Some of the different embodiments of connector-contact assemblies also include contact housings. It will be understood that, in addition to the combinations described below, the various connector contacts and contact housings can also be combined in different combinations not explicitly described to form other embodiments of connector-contact assemblies. Additionally, in at least some embodiments contact housings are combinable with housing-less connector-contact assemblies.

Figure 6A:
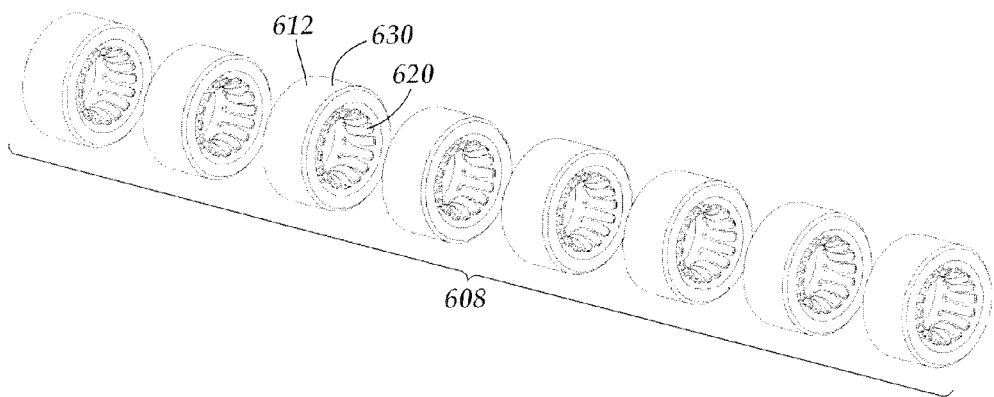
FIG. 6A is a schematic perspective view of one embodiment of multiple connector-contact assemblies arranged into an array suitable for use with the connector of FIG. 5, according to the invention.

FIG. 6A illustrates, in perspective view, one embodiment of multiple connector-contact assemblies, such as connector-contact assembly 612, arranged into an array 608 of connector-contact assemblies 612 suitable for disposing in the connector 544. When, as shown in FIG. 6A, multiple connector-contact assemblies 612 are arranged along the connector, multiple longitudinally-spaced-apart portions of the connector lumen may be formed by the multiple connector-contact assemblies 612.

The connector-contact assemblies 612 each include a connector contact 620. In at least some embodiments, the connector-contact assembly 612 includes a contact housing 630 covering at least a portion of the connector contact 620. The connector-contact assembly 612 defines a portion of the connector lumen (506 in FIG. 5).

Figure 6B:
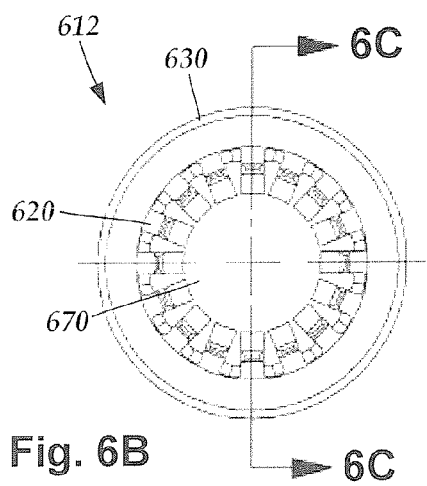
FIG. 6B is a schematic end view of one embodiment of one of the connector-contact assemblies of FIG. 6A, according to the invention.
Figure 6C:
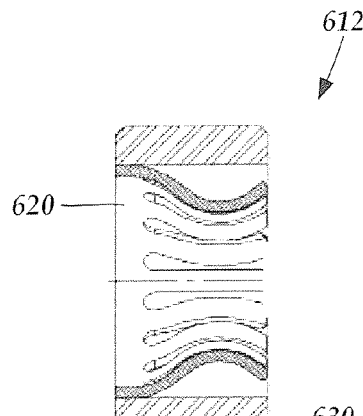
FIG. 6C is a schematic longitudinal cross-sectional view of one embodiment of the connector-contact assembly of FIG. 6B, according to the invention.
Figure 6D:
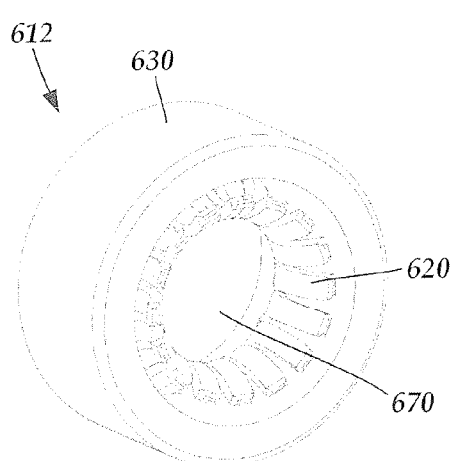
FIG. 6D is a schematic perspective view of one embodiment of the connector-contact assembly of FIG. 6B, according to the invention.

FIG. 6B illustrates, in end view, one embodiment of the connector-contact assembly 612. FIG. 6C illustrates, in longitudinal cross-sectional view, one embodiment of the connector-contact assembly 612. FIG. 6D illustrates, in perspective view, one embodiment of the connector-contact assembly 612. The connector-contact assembly 612 includes the connector contact 620 disposed in the contact housing 630. The connector contact 620 can remain disposed in the contact housing in any suitable manner including, for example, an interference fit, adhesive, welding, soldering, or the like or combinations thereof. In at least some embodiments, the connector contact 620 remains disposed in the contact housing solely by an interference fit.

The connector contact 620 can be formed from any electrically-conductive material suitable for implantation including, for example, one or more shape-memory materials, MP35N, stainless steel, or the like or combinations thereof. In at least some embodiments, the connector contact 620 and the contact housing 630 are both formed from electrically-conductive materials. In at least some embodiments, the connector contact 620 is disposed in the contact housing 630 such that the two are electrically coupled together. In which case, connector conductors (not shown) can be electrically coupled to the connector contacts 620 via their corresponding contact housings 630. It will be understood that the above materials and coupling techniques are applicable to any of the connector-contact assemblies described herein.

Figure 6E:
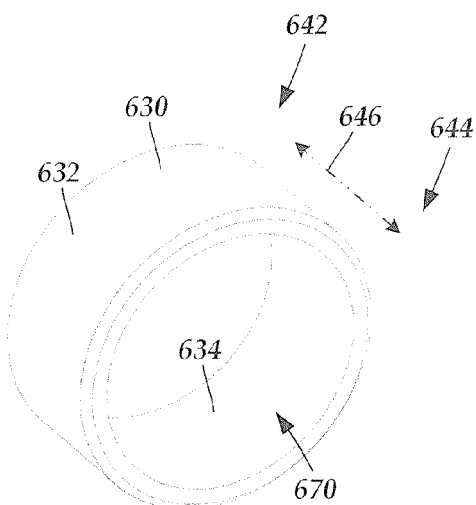
FIG. 6E is a schematic perspective view of one embodiment of the contact housing of the connector-contact assembly of FIG. 6D, according to the invention.
Figure 6F:
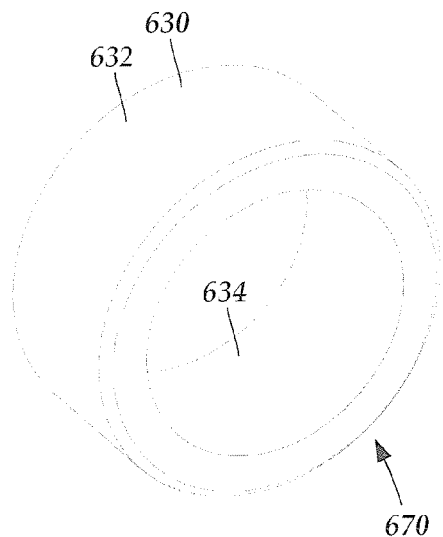
FIG. 6F is a schematic perspective view of another embodiment of the contact housing of the connector-contact assembly of FIG. 6D, according to the invention.
Figure 6G:
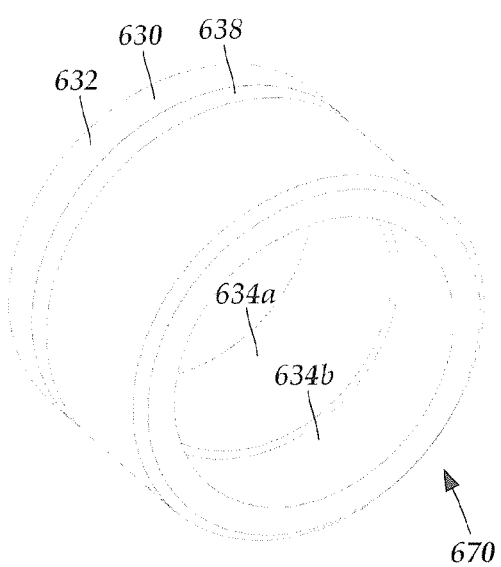
FIG. 6G is a schematic perspective view of yet another embodiment of the contact housing of the connector-contact assembly of FIG. 6D, according to the invention.

Turning to FIG. 6E, the contact housings 630 can be formed in any shape suitable for receiving a corresponding connector contact, such as the connector contact 620, and also suitable for being disposed in a connector, such as the connector 544 of FIG. 5. FIG. 6E illustrates, in perspective view, one embodiment of the contact housing 630. FIG. 6F illustrates, in perspective view, another embodiment of the contact housing 630. FIG. 6G illustrates, in perspective view, yet another embodiment of the contact housing 630.

The contact housings 630 shown in each of FIGS. 6E-6G are cylindrical, or substantially cylindrical, and each define an outer surface 632 and an inner surface 634. The contact housings 630 have first ends 642, opposing second ends 644 and longitudinal lengths 646.

The contact housings 630 each include an open center portion 670 defined by the inner surface 634 of the contact housing 630. The open center portions 670 are suitable for receiving connector contacts. In at least some embodiments, the open center portions 670 are suitable for receiving a single connector contact. In at least some embodiments, the open center portions 670 receive their corresponding connector contacts such that outer surfaces of the corresponding connector contacts directly abut the inner surfaces 634 of the contact housing 630.

The open center portions 670 can have either a constant diameter or a variable diameter. FIGS. 6E and 6F each show the open center portion 670 having a constant diameter. FIG. 6G shows the open center portion 670 having a first region 634a having a first diameter, and a second region 634b having a second diameter that is larger than the first diameter (see e.g., FIG. 9D). It may be advantageous to design the open center portion 670 to have two different diameters in order to control deformation of the connector contact (e.g., how far two ends of the connector contact can longitudinally separate from one another or be longitudinally squeezed together, how much the connector contact can expand radially, or some combination thereof) when a lead or lead extension is inserted into the open center portion 670 and straighten, or at least partially straighten, the biasing members.

In at least some embodiments, a connection region 638 is defined along the outer surface 632 of the contact housing 630. The connection region 638 may take any suitable form for facilitating making an electrical connection between the contact housing 630 and one or more connector conductors.

Figure 6H:
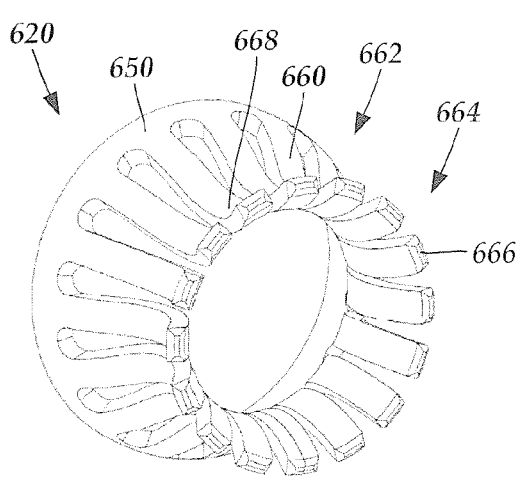
FIG. 6H is a schematic perspective view of one embodiment of the connector contact of the connector-contact assembly of FIGS. 6A-6D, according to the invention.

Turning to FIG. 6H, the connector contact uses biasing members to create and maintain electrical contact with terminals of an inserted elongated member. The biasing members may be biased radially-inward. In which case, when the biasing members are expanded radially outward when receiving the elongated member, the biasing of the biasing members maintains physical contact with the received elongated member. The biasing members may take any suitable form suitable for making electrical contact with an inserted elongated member. In at least some embodiments, the biasing members are formed as elongated strips of conductive, biased material. In at least some embodiments, the biasing members are formed as elongated strips of conductive, biased material that extend in a direction that is parallel to a longitudinal length of the elongated member. In at least some embodiments, the biasing members are formed as elongated strips of conductive, biased material that extend in a direction that is parallel to a longitudinal length of the connector housing.

In at least some embodiments, the biasing members are attached to a base. FIG. 6H illustrates, in perspective view, one embodiment of the connector contact 620. The connector contact 620 includes a base 650 and multiple biasing members, such as biasing member 660, attached to the base 650. The biasing members 660 include a proximal portion 662 attached to the base 650, an opposing distal portion 664 spaced away from the base 650, a distal tip 666 disposed along the distal portion 664, and one or more bends 668 disposed between the base 650 and the distal tip 666.

The base 650 can be any suitable shape having an outer circumference suitable for disposing in the open center portion 670 of the contact housing, and an inner circumference suitable for receiving the elongated member. In at least some embodiments, the base 650 is ring-shaped. In at least some embodiments, the base 650 forms a closed-loop of material. In at least some embodiments, the biasing members 660 each extend from one end of the base. In at least some embodiments, the biasing members 660 are equally-spaced along a circumference of the base 650.

The one or more bends 668 narrow the bore of the open center portion 670 to a diameter that is slightly less than a diameter of the elongated member insertable into the connector lumen (506 in FIG. 5). Thus, when the elongated member is inserted into the open center portion 670 and through the base 650, portions of the inserted elongated member contact the one or more bends 668 of the biasing members 660 and longitudinally expand the narrowed portion of the bore of the connector-contact lumen at the one or more bends 668. The biasing of the biasing members 660 facilitates the biasing members 660 maintaining physical contact with the inserted elongated member along, the bends 668.

Referring briefly back to FIG. 6C, in at least some embodiments the connector contacts 620 are disposed in the open center portions 670 such that the base 650 of the connector contact 620 is disposed along the first end 642 of the contact housing 630 and the biasing members 660 extend towards the second end 644 of the contact housing 630. In at least some embodiments, the base 650 is flush with the first end 642 of the contact housing 630. In at least some embodiments, the connector contacts 620 have lengths that are equal to the longitudinal length 646 of contact housing 630.

Figure 7A:
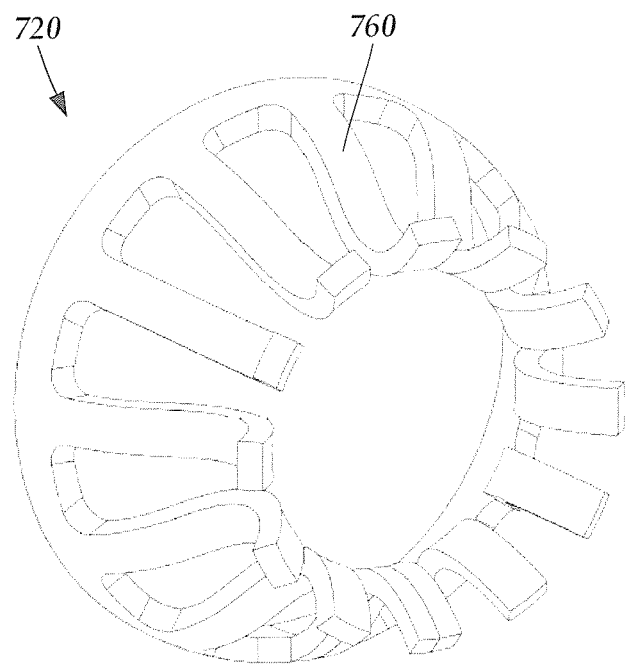
FIG. 7A is a schematic perspective view of another embodiment of a connector contact suitable for use with the connector-contact assembly of FIGS. 6A-6D, according to the invention.
Figure 7B:
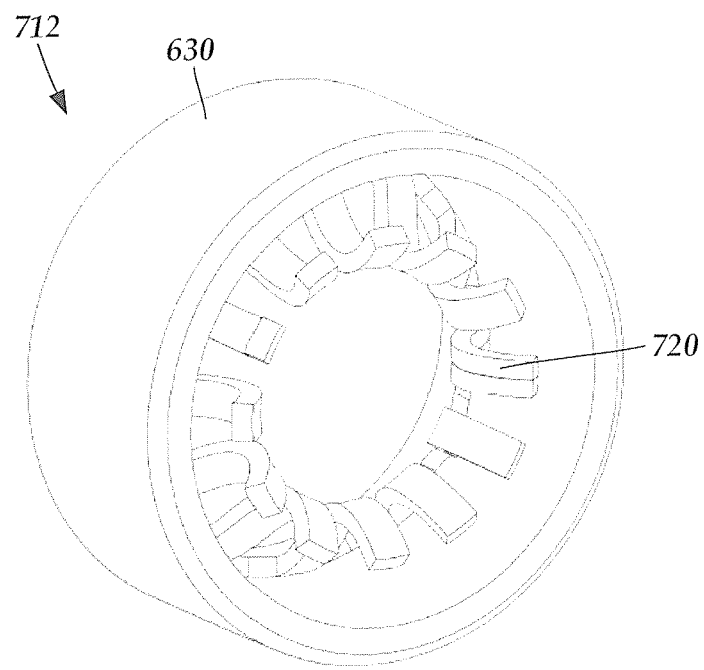
FIG. 7B is a schematic perspective view of one embodiment of a connector-contact assembly that includes the connector contact of FIG. 7A disposed in the contact housing of FIG. 6F, according to the invention.

Turning to FIG. 7A, the connector contact can have any suitable number of biasing members 660 including, for example, two, three, four, five, six, seven, eight, nine, ten, eleven, twelve, thirteen, fourteen, fifteen, sixteen, seventeen, eighteen, or more biasing members. FIG. 7A shows, in perspective view, one embodiment of a connector contact 720 having twelve biasing members 760. FIG. 7B shows, in perspective view, one embodiment of a connector-contact assembly 712 that includes the connector contact 720 disposed in the contact housing 630.

In at least some embodiments, the connector contact includes at least eight biasing members. In at least some embodiments, the connector contact includes no more than sixteen connector contacts. In at least some embodiments, the connector contact includes no less than eight and no more than sixteen biasing members. In FIGS. 6A, 6B, 6D, and 6H, the connector contact is shown having 16 biasing members.

Figure 8A:
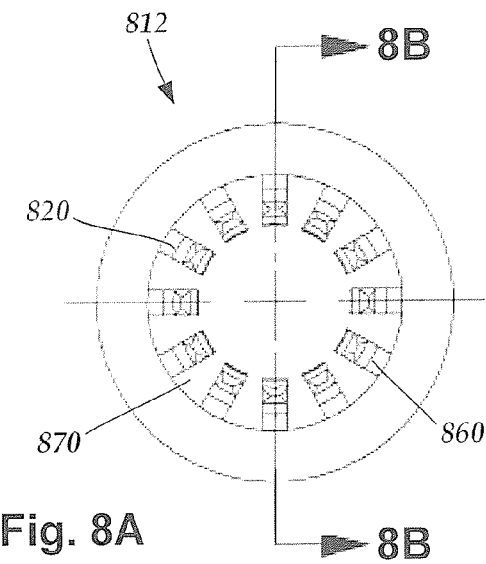
FIG. 8A is a schematic end view of another embodiment of a connector-contact assembly suitable for use with the connector of FIG. 5, according to the invention.

Turning to FIG. 8A, in at least some embodiments the connector-contact assembly is a single-piece assembly, where the connector contact and the contact housing are collectively formed from the same, single piece of material. In at least some embodiments, forming the connector-contact assembly as a single-piece assembly enables the connector contacts to be formed without bases. Instead, as shown in FIGS. 8A-8D, the biasing members may extend directly from the contact housing without directly contacting one another via a base.

Figure 8B:
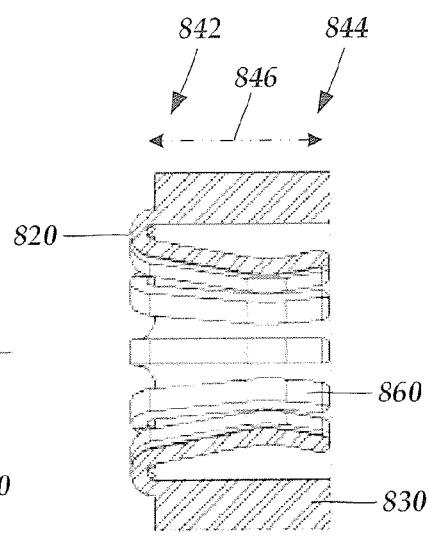
FIG. 8B is a schematic longitudinal cross-sectional view of one embodiment of the connector-contact assembly of FIG. 8A, according to the invention.
Figure 8C:
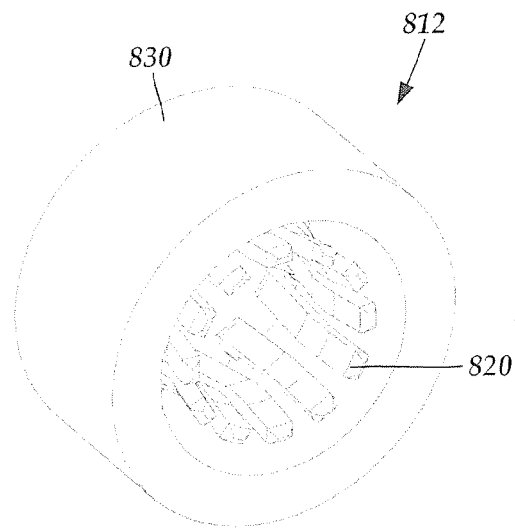
FIG. 8C is a schematic rear perspective view of one embodiment of the connector-contact assembly of FIG. 8A, according to the invention.

FIG. 8A illustrates, in end view, one embodiment of a connector-contact assembly 812. FIG. 8B illustrates, in longitudinal cross-sectional view, one embodiment of the connector-contact assembly 812. FIG. 8C illustrates, in rear perspective view, one embodiment of the connector-contact assembly 812. FIG. 8I) illustrates, in front perspective view, one embodiment of the connector-contact assembly 812. The connector-contact assembly 812 includes a connector contact 820 disposed in an open center portion 870 of a contact housing 830. As shown in FIGS. 8A-8D, the connector contact 820 and the contact housing 830 are collectively formed from a single piece of material.

Figure 8D:
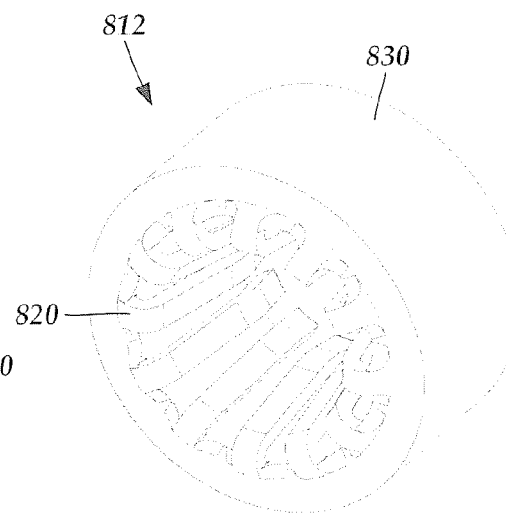
FIG. 8D is a schematic front perspective view of one embodiment of the connector-contact assembly of FIG. 8A, according to the invention.

The contact housing 630 has a first end 842, an opposing second end 844, and a longitudinal length 846. In FIGS. 8B and 8D, the biasing members are shown extending longitudinally away from the connector-contact assembly 812 (i.e., in a direction opposite to the second end 844 of the connector housing 630) beyond the first end 842 and bending back around to extend towards the second end 844 within the open center portion 870, thereby narrowing the open center portion 870 of the contact housing 830 enough to physically contact a portion of an elongated member, such as a lead or lead lumen, received by the open center portion 870. Thus, the biasing members 860 extend in two opposing directions. In at least some embodiments, the biasing members 860 extend the entire longitudinal length 846 of the contact housing 830 to the second end 844.

It may be advantageous for the biasing members 860, when formed from a single piece of material along with the contact housing, to be bent such that the biasing members extend beyond the first end of the contact housing and along two opposing longitudinal directions. The disclosed design may be easier to manufacture than a design where the biasing members only extend in a single longitudinal direction. The disclosed design may also be preferable to a design where the biasing members are folded back on themselves instead of being bent. Such a folded design may be unpredictable in function and may wear out prematurely, as compared to a bent design.

Figure 9A:
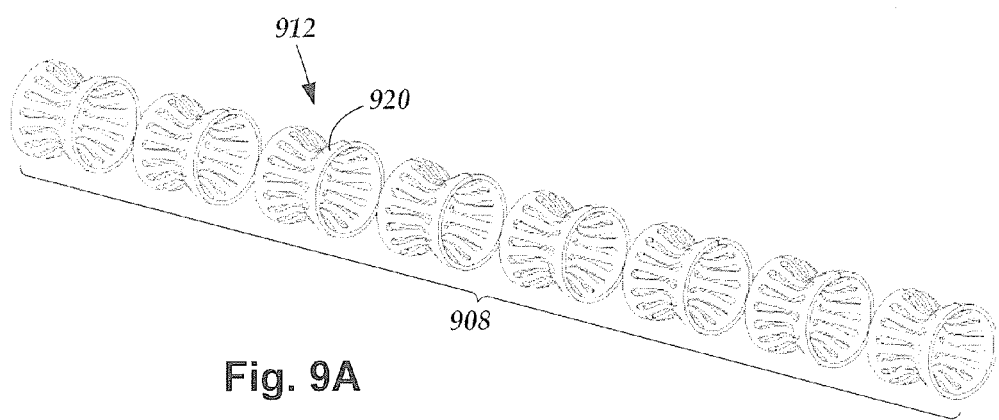
FIG. 9A is a schematic perspective view of another embodiment of multiple connector-contact assemblies arranged into an array suitable for use with the connector of FIG. 5, according to the invention.

Turning to FIG. 9A, in at least some embodiments the connector contacts includes bases disposed along two opposing ends of the connector contacts. In some embodiments, the leaf-spring contacts are attached to both bases. In other embodiments, the leaf-spring contacts are attached to only one of the two bases. In some embodiments, the connector-contact assemblies include connector housings. In other embodiments, the connector-contact assemblies do not include contact housings (i.e., the connector-contact assemblies are housing-less).

FIG. 9A illustrates, in perspective view, one embodiment of multiple connector-contact assemblies, such as connector-contact assembly 912, arranged into an array 908 of connector-contact assemblies 912. The connector-contact assemblies 912 each include a connector contact 920. The connector-contact assemblies 912 shown in FIG. 9A do not include contact housings.

Figure 9B:
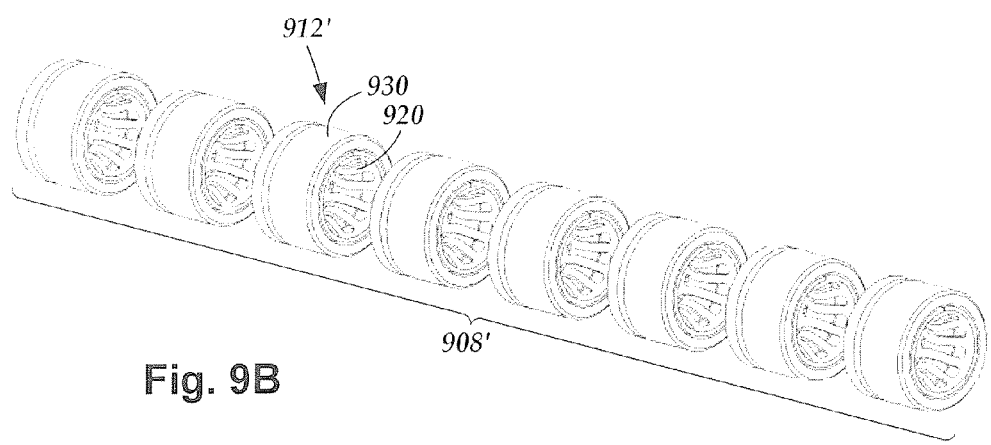
FIG. 9B is a schematic perspective view of yet another embodiment of multiple connector-contact assemblies arranged into an array suitable for use with the connector of FIG. 5, according to the invention.

FIG. 9B illustrates, in perspective view, another embodiment of multiple connector-contact assemblies, such as connector-contact assembly 912', arranged into an array 908' of connector-contact assemblies 912'. The connector-contact assemblies 912' each include the connector contact 920. The connector-contact assemblies 912' shown in FIG. 9B each include a contact housing 930 covering at least a portion of the connector contact 920.

Figures 9C, 9D:
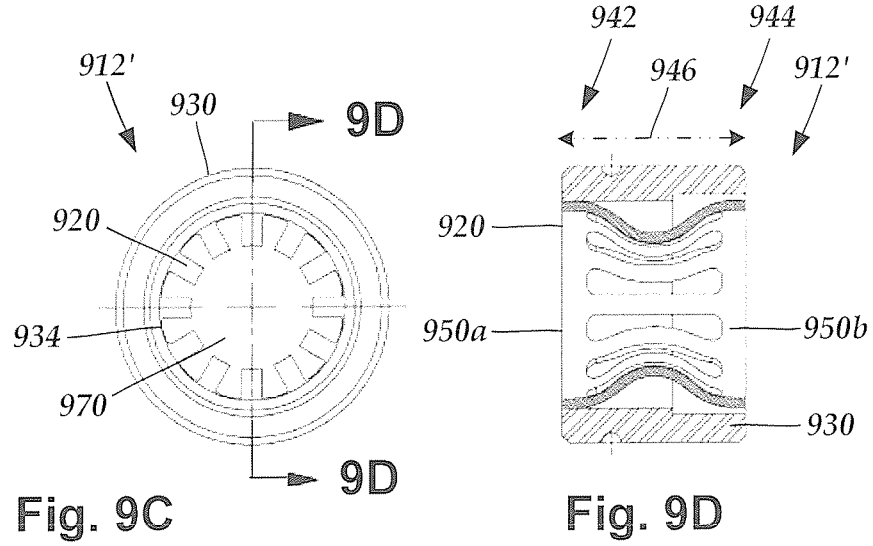
FIG. 9C is a schematic end view of one embodiment of one of the connector-contact assemblies of FIG. 9B, according to the invention.
FIG. 9D is a schematic longitudinal cross-sectional view of one embodiment of the connector-contact assembly of FIG. 9C, according to the invention.

FIG. 9C illustrates, in end view, one embodiment of one of the connector-contact assembles 912', as shown in FIG. 9B. FIG. 9D illustrates, in longitudinal cross-sectional view, one embodiment of the connector-contact assembly 912'. The contact housing 930 has a first end portion 942, an opposing second end portion 944, and a longitudinal length 946. A first base 950a is disposed along the first end portion 942 and a second base 950b is disposed along the second end portion 944. In at least some embodiments, the first end portion has a first inner diameter, and the second end portion has a second inner diameter that is larger than the first inner diameter (see e.g., FIG. 6G).

Figure 9E:
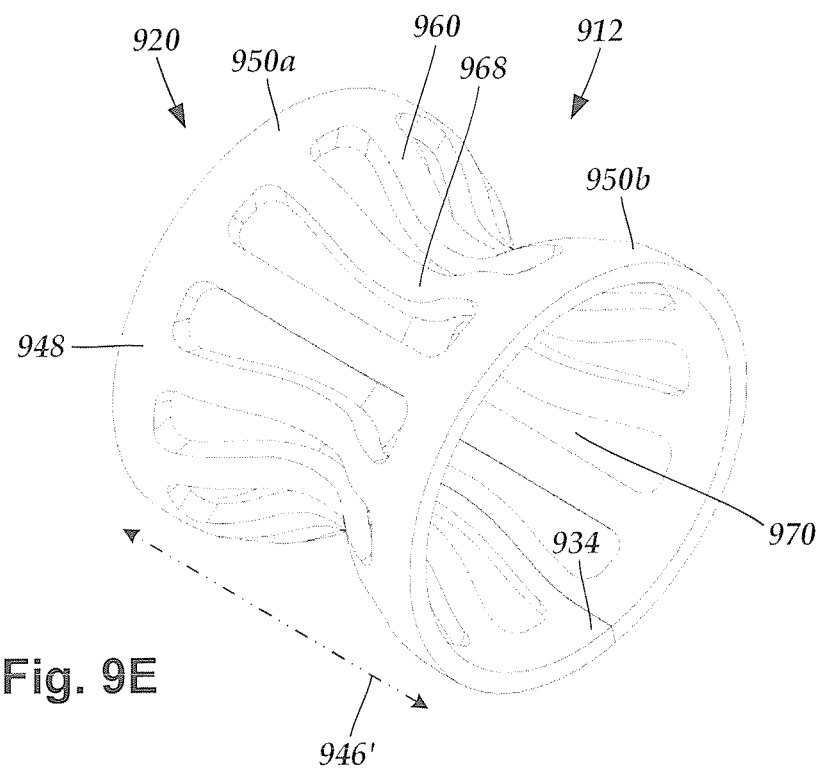
FIG. 9E is a schematic perspective view of one embodiment of one connector-contact assembly of the array of connector-contact assemblies of FIGS. 9A and 9B, according to the invention.

FIG. 9E illustrates, in perspective view, one embodiment of the connector contact 920 of either the connector-contact assemblies 912 of FIG. 9A, or the connector-contact assemblies 912' of FIG. 9B. The connector contact 920 includes the first base 950a and the second base 950b disposed along opposing ends of the connector contact 920. Multiple biasing members 960 attach the first base 950a to the second base 950b. The biasing members 960 each include at least one bend 968 that narrows at least one portion of an open center portion 970 extending along a longitudinal length 946' of a body 948 of the connector contact 920. Note that, the inner walls of the connector housing may provide a rigid surface to limit radial expansion of the connector contact.

Note also that, in housing-less embodiments of the connector-contact assembly, such as the connector-contact assembly 912, the open center portion 970 is defined by inner surfaces 934 of the connector contact 920, instead of an inner surface of a connector housing, such as for connector-contact assembly 912'. In which case, the walls of the connector lumen (506 in FIG. 5) may provide a rigid surface to control the amount of radial expansion of one or more portions of the connector-contact assembly (e.g., the biasing members 960 along the bend 968) when an elongated member is received.

Note further that, radial expansion of the biasing members 960 along the bend 968 may cause a corresponding longitudinal expansion of the connector-contact assembly, thereby increasing the longitudinal distance between the two bases 950a and 950b. As discussed above, with reference to FIG. 6G, the longitudinal expansion of the connector-contact assembly may be controlled by using a contact housing with an open center portion having two different diameters. Thus, one of the bases 950a or 950b can be disposed in the portion of the contact housing having the larger of the two diameters and be limited in longitudinal movement. Additionally, disposing one of the two bases in the larger-diameter portion of a multi-diameter contact housing may limit the amount that the connector contact can be longitudinally squeezed together during insertion of the elongated member into the open center portion 970.

At least one of the first base 950a or the second base 950b may be formed as a closed-loop of material. This may be particularly beneficial in embodiments that do not include contact housings, such as connector-contact assembly 912. In which case, the closed-loop design may prevent, or at least significantly reduce, undesired changes in shape to the connector-contact assembly (e.g., radially-outward expansion of the bases, twisting of the biasing members) when a lead or lead extension is disposed in the connector contact.

Figure 10A:
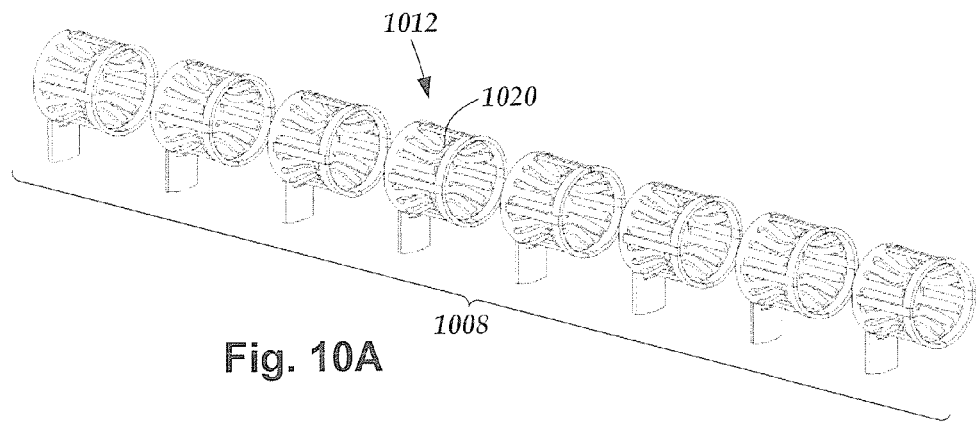
FIG. 10A is a schematic perspective view of still yet another embodiment of multiple connector-contact assemblies arranged into an array suitable for use with the connector of FIG. 5, according to the invention.

Turning to FIG. 10A, in at least some embodiments the bases of the connector contacts are disposed along two opposing ends of the connector contacts, while the leaf-spring contacts of the connector contact are attached to only one of the two bases. In at least some embodiments, the connector-contact assemblies are housing-less.

FIG. 10A illustrates, in perspective view, one embodiment of multiple connector-contact assemblies, such as connector-contact assembly 1012, arranged into an array 1008 of connector-contact assemblies 1012. The connector-contact assemblies 1012 include a connector contact 1020. The connector-contact assemblies 1012 shown in FIG. 10A do not include contact housings.

Figure 10B:
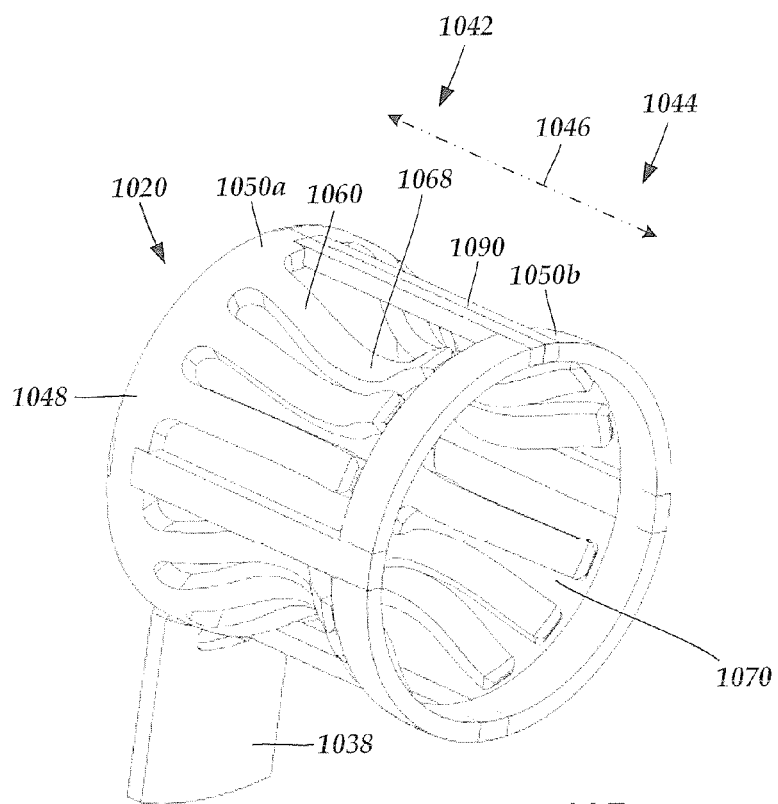
FIG. 10B is a schematic perspective view of one embodiment of one connector-contact assembly of the array of connector-contact assemblies of FIG. 10A, according to the invention.

FIG. 10B illustrates, in perspective view, one embodiment of the connector contact 1020 of the connector-contact assembly 1012. The connector contact 1020 has a first end portion 1042, an opposing second end portion 1044, and a longitudinal length 1046. A first base 1050a is disposed along the first end portion 1042 and a second base 1050b is disposed along the second end portion 1044.

Multiple connector supports, such as connector support 1090, extend along the longitudinal length 1046 of the connector contact 1020 and attach the first base 1050a to the second base 1050b. In at least some embodiments, the connector supports 1090 are rigid to prevent undesired changes in shape to the connector contact (e.g., longitudinally-outward expansion of the bases) when a lead or lead extension is disposed in the connector contact.

Multiple biasing members 1060 are attached to the first base 1050a and extend towards the second base 1050b. The biasing members 960 each include at least one bend 1068 that narrows at least one portion of an open center portion 1070 extending along the longitudinal length 1046 of a body 1048 of the connector contact. The biasing members 1060 do not attach to the second base 1050b. When the biasing members 1060 are attached to the first base 1050a without being attached to the second base 1050b, the biasing members 1060 are able to at least partially straighten along the at least one bend 1068 when receiving an inserted lead or lead extension, thereby utilizing the bias of the biasing members to maintain contact with the received lead or lead extension.

At least one of the first base 1050a or the second base 1050b may, optionally, be formed as closed-loops of material to prevent undesired changes in shape to the connector contact (e.g., radially-outward expansion of the bases, twisting of the biasing members) when a lead or lead extension is disposed in the connector contact. In at least some embodiments, the connector-contact assembly 1012 includes a connection region 1038 formed along the connector contact 1020. The connection region 1038 may take any suitable form for facilitating making an electrical connection between the connector contact 1020 and one or more connector conductors. In FIG. 10B, the connection region 1038 is shown as a tab.

Figure 11A:
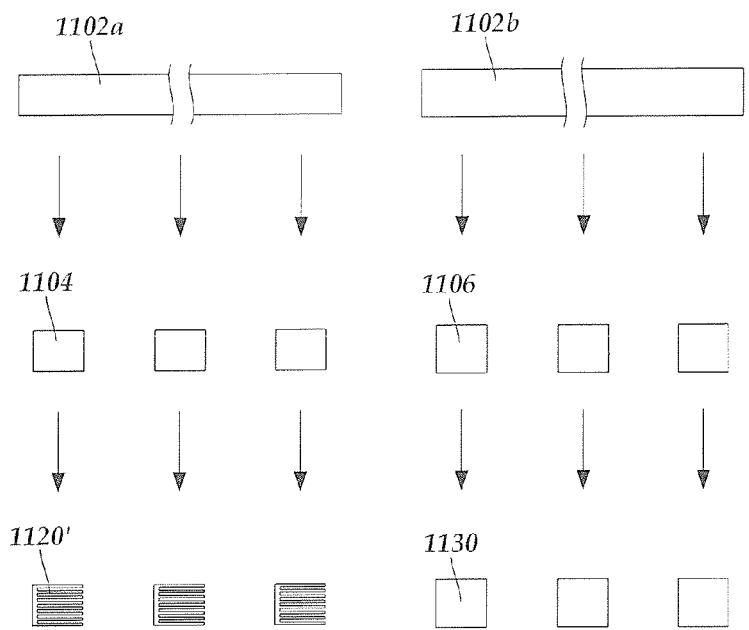
FIG. 11A is a schematic side view of one embodiment of pre-connector contacts and contact housings formed from tubing, according to the invention.
Figure 11B:
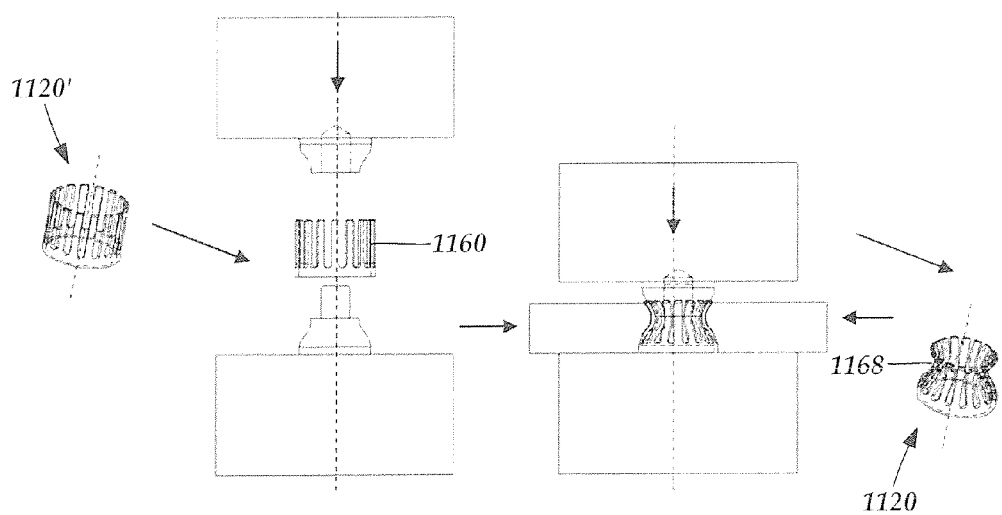
FIG. 11B is a schematic view of one embodiment of the pre-connector contact of FIG. 11A being re-shaped to form a connector contact, according to the invention.
Figure 11C:
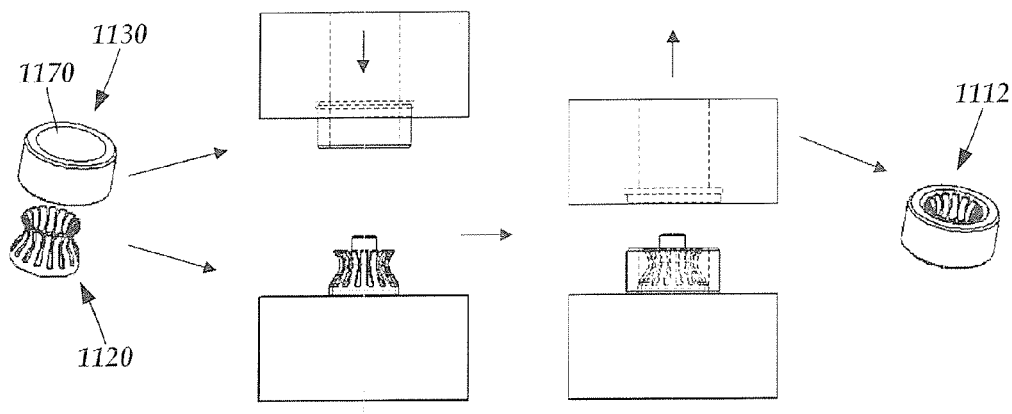
FIG. 11C is a schematic view of one embodiment of the connector contact of FIG. 11B being inserted into an open center portion of the contact housing of FIG. 11A to form a connector-contact assembly, according to the invention.
Figure 12:
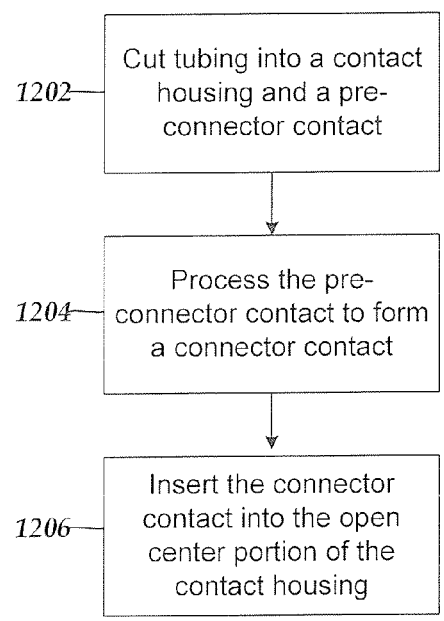
FIG. 12 is a control-flow diagram showing one embodiment of a technique for forming connector-contact assemblies, according to the invention.

Turning to FIGS. 11A-12, the above-described connector-contact assemblies may be manufactured using any suitable technique. In at least some embodiments, the connector-contact assemblies are formed from electrically-conductive tubing. It may be advantageous to form the connector-contact assemblies from tubing, rather than from flat sheets of material. Forming the connector-contact assemblies from tubing may be less expensive than forming the connector-contact assemblies from flat sheets of material.

Moreover, forming the connector-contact assemblies from tubing removes the seams that are inherent in techniques that involve forming, the connector-contact assemblies from flat sheets of material. When flat sheets of metal are bent to form cylinders, a seam is formed along the opposing edges of the sheets of material that extend along a lengths of both the connector contact and the contact housing. The seams may prevent an interference fit from being formable between the connector contact and the contact housing.

FIG. 11A illustrates, in side view, one embodiment of pre-connector contacts and contact housings, such as pre-connector contact 1120' and contact housing 1130, respectively, formed from tubing 1102a and 1102b, respectfully. In FIG. 11A, the tubing 1102a is shown cut transversely into multiple cylindrical first pre-components, such as a first pre-component 1104, and tubing 1102b is show cut transversely into multiple cylindrical second pre-components, such as second pre-component 1106. The first pre-components 1104 are shown in FIG. 11A being further cut to form pre-connector contacts 1120' and the second pre-components 1106 are shown being further cut to form contact housings 1130.

The tubing 1102a and 1102b can be cut into first pre-components 1104 and second pre-components 1106, respectively; and the first pre-components 1104 and the second pre-components 1106 can be cut into pre-connector contacts 1120' and contact housings 1130, respectively, using any suitable techniques including, for example, laser cutting, machining, or the like or combinations thereof.

In some embodiments, the tubing 1102b has an inner diameter that is equal to, or slightly larger than, an outer diameter of the tubing 1102a. This may be advantageous to facilitate manufacture so that, as shown below with reference to FIG. 11C, connector contacts 1120 formed from the pre-connector contact 1120' are insertable into open center portions of the contact housings 1130. In other embodiments, the manufacturing process has an additional step to alter one or more diameters of at least one of the tubing 1102a, tubing 1102b, first pre-component 1104, second pre-component 1106, pre-connector contact 1120', connector contact 1120, or contact housing 1130 so that the connector contact 1120 has an outer diameter that is equal to, or slightly smaller than, an inner diameter of the contact housing 1130.

FIG. 11B illustrates, in schematic side view, one embodiment of the pre-connector contact 1120' being further processed to form a connector contact 1120. In at least some embodiments, the further processing of the pre-connector contact 1120' includes forming at least one bend 1168 in the biasing, members 1160. In at least some embodiments, the further processing of the pre-connector contact 1120' includes re-shaping the biasing members 1160.

As mentioned above, the connector contacts and contact housings can be formed from any electrically-conductive material suitable for implantation including, for example, one or more shape-memory materials, MP35N, stainless steel, or the like or combinations thereof. In the case of shape-memory materials, such as Nitinol, the material may additionally need to be shape set; which may include heating the components to 500°-550° C. and quenching in water.

FIG. 11C illustrates, in schematic, side view, one embodiment of the connector contact 1120 being inserted into the open center portion 1170 of the connector housing 1130 to form a connector-contact assembly 1112. In at least some embodiments, the connector contact 1120 is pressed into the open center portion 1170 of the connector housing 1130. In some embodiments, the connector contact 1120 remains in the open center portion 1170 of the connector housing 1130 solely by an interference fit. In other embodiments, the connector contact 1120 is welded, soldered, adhesively-affixed, or the like, to the connector housing 1130 instead of, or in addition to, an interference fit.

The technique described above, with reference to FIGS. 11A-11C may further include inserting the connector-contact assembly into the connector (see e.g., 544 of FIG. 5). Insertion of the connector-contact assembly into the connector may involve forming an opening along the connector suitable for inserting the connector-contact assembly through, and applying electrically-insulative material to patch the opening subsequent to insertion of the connector-contact assembly into the connector. Additionally, the connector-contact assembly may be electrically-coupled to one or more connector conductors.

FIG. 12 is a control-flow diagram showing one embodiment of steps for forming a connector-contact assembly. In step 1202, tubing is cut into contact housings and pre-conductor contacts. In step 1204, the pre-connector contacts are processed into connector contacts. In step 1206, the connector contacts are inserted into the contact housings.

Figure 13:
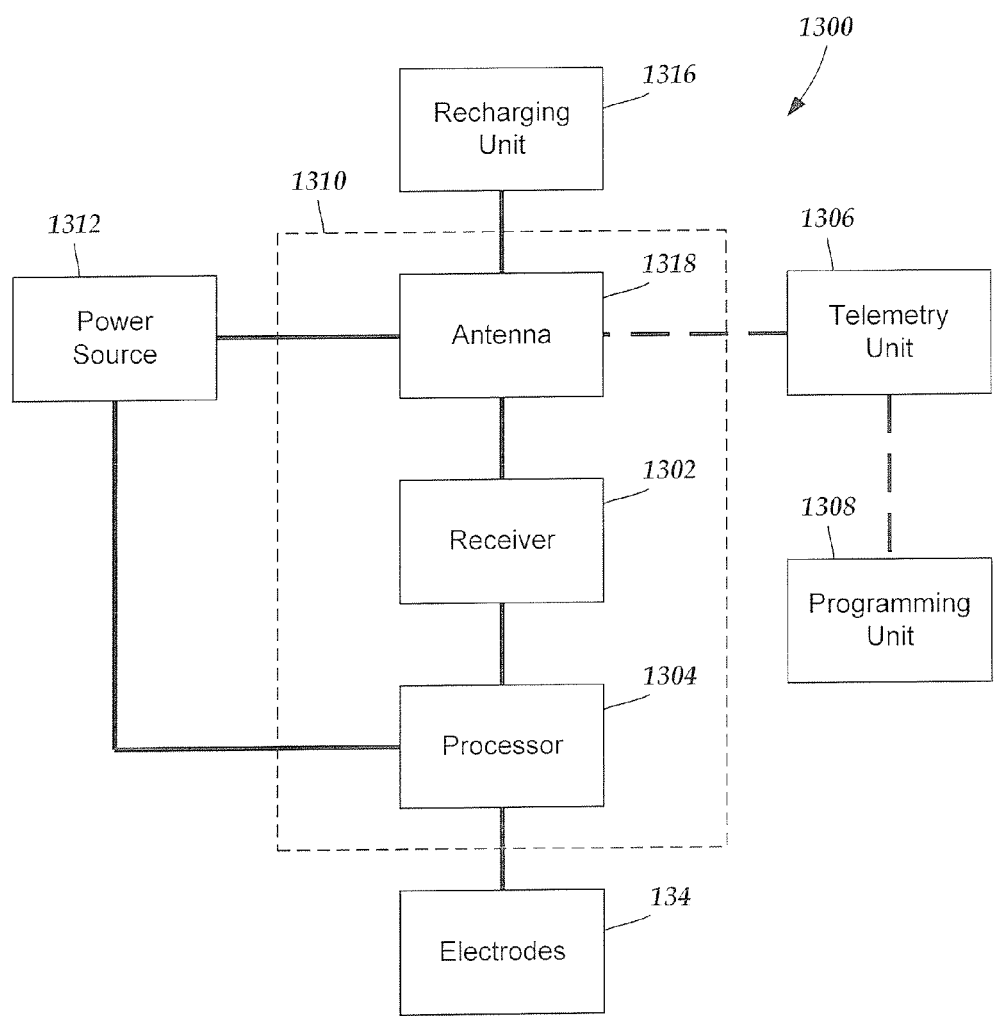
FIG. 13 is a schematic overview of one embodiment of components of an electrical stimulation system, according to the invention.

FIG. 13 is a schematic overview of one embodiment of components of an electrical stimulation system 1300 including an electronic subassembly 1310 disposed within a control module. It will be understood that the electrical stimulation system can include more, fewer, or different components and can have a variety of different configurations including those configurations disclosed in the stimulator references cited herein.

Some of the components (for example, power source 1312, antenna 1318, receiver 1302, and processor 1304) of the electrical stimulation system can be positioned on one or more circuit boards or similar carriers within a sealed housing of an implantable pulse generator, if desired. Any power source 1312 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 1318 or a secondary antenna. The external power source can be in a device that is mounted on the skin of the user or in a unit that is provided near the user on a permanent or periodic basis.

If the power source 1312 is a rechargeable battery, the battery may be recharged using the optional antenna 1318, if desired. Power can be provided to the battery for recharging by inductively coupling the battery through the antenna to a recharging unit 1316 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1304 is generally included to control the timing and electrical characteristics of the electrical stimulation system. For example, the processor 1304 can, if desired, control one or more of the timing, frequency, strength, duration, and waveform of the pulses. In addition, the processor 1304 can select which electrodes can be used to provide stimulation, if desired. In some embodiments, the processor 1304 may select which electrode(s) are cathodes and which electrode(s) are anodes. In some embodiments, the processor 1304 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1308 that, for example, allows modification of pulse characteristics. In the illustrated embodiment, the processor 1304 is coupled to a receiver 1302 which, in turn, is coupled to the optional antenna 1318. This allows the processor 1304 to receive instructions from an external source to, for example, direct the pulse characteristics and the selection of electrodes, if desired.

In one embodiment, the antenna 1318 is capable of receiving signals (e.g., RF signals) from an external telemetry unit 1306 which is programmed by a programming unit 1308. The programming unit 1308 can be external to, or part of, the telemetry unit 1306. The telemetry unit 1306 can be a device that is worn on the skin of the user or can be carried by the user and can have a form similar to a pager, cellular phone, or remote control, if desired. As another alternative, the telemetry unit 1306 may not be worn or carried by the user but may only be available at a home station or at a clinician's office. The programming unit 1308 can be any unit that can provide information to the telemetry unit 1306 for transmission to the electrical stimulation system 1300. The programming unit 1308 can be part of the telemetry unit 1306 or can provide signals or information to the telemetry unit 1306 via a wireless or wired connection. One example of a suitable programming unit is a computer operated by the user or clinician to send signals to the telemetry unit 1306.

The signals sent to the processor 1304 via the antenna 1318 and receiver 1302 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1300 to cease operation, to start operation, to start charging the battery, or to stop charging the battery. In other embodiments, the stimulation system does not include an antenna 1318 or receiver 1302 and the processor 1304 operates as programmed.

Optionally, the electrical stimulation system 1300 may include a transmitter (not shown) coupled to the processor 1304 and the antenna 1318 for transmitting signals back to the telemetry unit 1306 or another unit capable of receiving the signals. For example, the electrical stimulation system 1300 may transmit signals indicating whether the electrical stimulation system 1300 is operating properly or not or indicating when the battery needs to be charged or the level of charge remaining in the battery. The processor 1304 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A connector for an implantable electrical medical device, the connector comprising:
    an elongated connector housing having a first end and an opposing second end;
    a connector lumen defined in the connector housing, the connector lumen configured and arranged for receiving a proximal portion of a lead or lead extension;
    a plurality of connector-contact assemblies disposed in the connector lumen, the plurality of connector-contact assemblies each configured and arranged to couple to at least one of a plurality of terminals disposed on the proximal portion of the lead or lead extension when the proximal portion of the lead or lead extension is received by the connector lumen, each of the plurality of connector-contact assemblies comprising
        a contact body having a first end, an opposing second end, an inner surface, and an outer surface, the inner surface of the contact body defining an open center portion having an inner diameter, the contact body comprising,
            a first base disposed along the first end of the contact body,
            a second base disposed along the second end of the contact body and coupled to the first base,
            a plurality of biasing members attached to the first base and extending towards the second base, wherein the biasing members are not attached to the second base, wherein when the proximal portion of the lead on lead extension is received by the connector lumen the plurality of biasing members physically contact the received lead or lead extension, and
            a plurality of rigid support members extending between the first and second bases and directly attached to both the first and second bases; and
    a plurality of connector conductors coupled to the plurality of connector-contact assemblies and extending along the connector housing.

2. The connector of claim 1, wherein each of the plurality of connector-contact assemblies comprises at least eight biasing members.

3. The connector of claim 1, wherein each of the plurality of connector-contact assemblies comprises no more than sixteen biasing members.

4. The connector of claim 1 wherein, for each of the plurality of connector-contact assemblies, the biasing members each comprise at least one bend that extends into the open center portion of the contact body and that narrows the inner diameter of the open center portion.

5. A lead assembly comprising:
    a lead comprising
        a lead body with a proximal portion, a distal portion, and a longitudinal length,
        a plurality of electrodes disposed on the distal portion of the lead body,
        a plurality of terminals disposed on the proximal portion of the lead body, and
        a plurality of lead conductors electrically coupling the plurality of electrodes to the plurality of terminals;
    a lead extension having a proximal portion and a distal portion; and
    the connector of claim 1 disposed along the distal portion of the lead extension;
    wherein the proximal portion of the lead body is configured and arranged for insertion into the connector lumen of the connector.

6. An electrical stimulating system comprising:
the lead assembly of claim 5; and
a control module coupleable to the proximal portion of the lead extension of the lead assembly, the control module comprising
a housing, and
an electronic subassembly disposed in the housing.

7. An electrical stimulating system comprising:
a lead comprising
a lead body with a proximal portion, a distal portion, and a longitudinal length,
a plurality of electrodes disposed along the distal portion of the lead body,
a plurality of terminals disposed along the proximal portion of the lead body, and
a plurality of lead conductors electrically coupling the plurality of electrodes to the plurality of terminals;
a control module electrically coupleable to the lead, the control module comprising
a housing, and
an electronic subassembly disposed in the housing; and
the connector of claim 1 coupled directly to the control module;
wherein the proximal portion of the lead body is configured and arranged for insertion into the connector lumen of the connector.

8. The connector of claim 1, wherein the first base and the second base are each closed loops with the biasing members disposed entirely between the first and second bases.

9. The connector of claim 1, wherein each of the connector-contact assemblies does not include a contact housing.

10. The connector of claim 1, wherein the plurality of rigid support members comprises two rigid support members disposed opposite each other.

11. The connector of claim 1, wherein the plurality of rigid support members comprises four rigid support members disposed at equal intervals around the first base.

12. The connector of claim 1, wherein the plurality of rigid support members consists of four rigid support members disposed at equal intervals around the first base.

13. The connector of claim 1, wherein each of the rigid support members is a bar attaching the first base to the second base.

14. A connector for an implantable electrical medical device, the connector comprising:
an elongated connector housing a first end and an opposing second end;
a connector lumen defined in the connector housing, the connector lumen configured and arranged for receiving a proximal portion of a lead or lead extension;
a plurality of connector-contact assemblies disposed in the connector lumen, the plurality of connector-contact assemblies each configured and arranged to couple to at least one of a plurality of terminals disposed on the proximal portion of the lead or lead extension when the proximal portion of the lead or lead extension is received by the connector lumen, each of the plurality of connector-contact assemblies comprising
a contact body having a first end, an opposing second end, an inner surface, and an outer surface, the inner surface of the contact body defining an open center portion having an inner diameter, the contact body comprising,
a first base disposed along the first end of the contact body,
a second base disposed along the second end of the contact body and coupled to the first base,
a plurality of biasing members attached to the first base and extending towards the second base, wherein the biasing members are not attached to the second base, wherein when the proximal portion of the lead or lead extension is received by the connector lumen the plurality of biasing members physically contact the received lead or lead extension, and
a plurality of right support members extending between the first and second bases and directly attached to both the first and second bases; and
a plurality of connectors conductors coupled to the plurality of connector-contact assemblies and extending along the connector housing,
wherein each of the connector-contact assemblies further comprises a tab extending from the contact body to facilitate making an electrical connection between the connector-contact assembly and a one of the connector conductors.

15. The connector of claim 14, wherein the tab extends from either the first base or the second base.

16. The connector of claim 14, wherein, for each of the plurality of connector-contact assemblies, the biasing members each comprise at least one bend that extends into the open center portion of the contact body and that narrows the inner diameter of the open center portion.

17. The connector of claim 14, wherein the first base and the second base are each closed loops with the biasing members disposed entirely between the first and second bases.

18. A lead assembly comprising:
a lead comprising
a lead body with a proximal portion, a distal portion, and a longitudinal length,
a plurality of electrodes disposed on the distal portion of the lead body,
a plurality of terminals disposed on the proximal portion of the lead body, and
a plurality of lead conductors electrically coupling the plurality of electrodes to the plurality of terminals;
a lead extension having a proximal portion and a distal portion; and
the connector of claim 14 disposed along the distal portion of the lead extension;
wherein the proximal portion of the lead body is configured and arranged for insertion into the connector lumen of the connector.

19. An electrical stimulating system comprising:
the lead assembly of claim 18; and
a control module coupleable to the proximal portion of the lead extension of the lead assembly, the control module comprising
a housing, and
an electronic subassembly disposed in the housing.

20. An electrical stimulating system comprising:
a lead comprising
a lead body with a proximal portion, a distal portion, and a longitudinal length,
a plurality of electrodes disposed along the distal portion of the lead body,
a plurality of terminals disposed along the proximal portion of the lead body, and
a plurality of lead conductors electrically coupling the plurality of electrodes to the plurality of terminals;
a control module electrically coupleable to the lead, the control module comprising a housing, and
an electronic subassembly disposed in the housing; and the connector of claim 14 coupled directly to the control module;

wherein the proximal portion of the lead body is configured and arranged for insertion into the connector lumen of the connector.

\* \* \* \* \*